United States Patent
Suzuki

(10) Patent No.: US 9,462,982 B2
(45) Date of Patent: Oct. 11, 2016

(54) IMAGING STAND

(71) Applicant: KONICA MINOLTA, INC., Chiyoda-ku (JP)

(72) Inventor: Atsushi Suzuki, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 14/637,072

(22) Filed: Mar. 3, 2015

(65) Prior Publication Data

US 2015/0252938 A1    Sep. 10, 2015

(30) Foreign Application Priority Data

Mar. 5, 2014  (JP) .................................. 2014-042286

(51) Int. Cl.
*H05G 1/02*     (2006.01)
*A61B 6/00*     (2006.01)

(52) U.S. Cl.
CPC ........... *A61B 6/4233* (2013.01); *A61B 6/4283* (2013.01); *A61B 6/4429* (2013.01); *A61B 6/547* (2013.01); *A61B 6/40* (2013.01); *A61B 6/542* (2013.01); *A61B 6/588* (2013.01)

(58) Field of Classification Search
CPC ........................ A61B 6/4441; G03B 42/025
USPC ............ 248/161, 162.1, 411, 157, 420, 422; 378/193, 195, 196, 197
See application file for complete search history.

(56) References Cited

U.S. PATENT DOCUMENTS

| | | | | |
|---|---|---|---|---|
| 2,598,529 A | * | 5/1952 | Fritz | G03B 42/025 248/124.2 |
| 3,671,745 A | * | 6/1972 | Fouquart | A61B 6/032 378/155 |
| 4,602,378 A | * | 7/1986 | Kelman | A61B 6/4283 378/181 |
| 4,627,591 A | * | 12/1986 | Heckmann | A47B 9/06 108/148 |
| 4,752,948 A | * | 6/1988 | MacMahon | A61B 6/4405 378/193 |

(Continued)

FOREIGN PATENT DOCUMENTS

| | | |
|---|---|---|
| JP | H06-342099 | 12/1994 |
| JP | H09-073144 | 3/1997 |

(Continued)

*Primary Examiner* — Terrell McKinnon
*Assistant Examiner* — Michael McDuffie
(74) *Attorney, Agent, or Firm* — Cozen O'Connor

(57) ABSTRACT

An imaging stand includes: a holder configured to hold an installed cassette-type detector; a supporting member configured to support the holder from a back surface side; a circular gear secured to a shaft member protruding from a rotation center of the holder toward the supporting member on the back surface side, the holder being located in a different position from a position corresponding to the center of a radiation incidence surface of the cassette-type detector held in the holder; and a linear gear having concavities and convexities to be engaged with teeth of the circular gear, the linear gear being attached to the supporting member, wherein, when the holder holding the cassette-type detector is rotated relative to the supporting member, the rotation center of the holder linearly moves relative to the supporting member as the holder rotates, and a change is caused in orientation and position of the cassette-type detector.

10 Claims, 28 Drawing Sheets

(56) References Cited

U.S. PATENT DOCUMENTS

| | | | | |
|---|---|---|---|---|
| 5,143,333 | A * | 9/1992 | Warden | A61B 6/447 248/123.11 |
| 6,702,459 | B2 * | 3/2004 | Barnes | A61B 6/4405 250/522.1 |
| 6,707,880 | B2 | 3/2004 | Yamayoshi | |
| 6,851,851 | B2 * | 2/2005 | Smith | A61B 6/0457 378/167 |
| 6,890,099 | B2 * | 5/2005 | Tanaka | A61B 6/08 378/197 |
| 7,125,164 | B2 * | 10/2006 | Sekol | A61B 6/00 378/167 |
| 7,163,184 | B2 * | 1/2007 | Nielsen | A47B 9/20 108/147 |
| 7,165,885 | B2 * | 1/2007 | Lumma | A61B 6/4464 378/167 |
| 7,185,868 | B2 * | 3/2007 | Wang | A47F 5/04 248/125.1 |
| 7,306,368 | B2 * | 12/2007 | Isono | A61B 6/00 378/181 |
| 7,395,565 | B2 * | 7/2008 | Zhang | A61B 6/04 248/425 |
| 7,545,914 | B2 | 6/2009 | Kito et al. | |
| 7,806,591 | B2 | 10/2010 | Wang et al. | |
| 7,984,889 | B2 * | 7/2011 | Whitley | F16M 11/06 248/221.11 |
| 8,899,832 | B2 * | 12/2014 | Fabrizio | A61B 6/08 378/195 |
| 8,956,045 | B2 * | 2/2015 | Tajima | A61B 6/4283 378/145 |
| 2003/0164431 | A1 * | 9/2003 | Kanashiki | A47B 97/04 248/157 |
| 2003/0190014 | A1 * | 10/2003 | Nakagawa | A61B 6/4405 378/193 |
| 2007/0086577 | A1 * | 4/2007 | Kobayashi | A61B 6/0457 378/195 |
| 2008/0099637 | A1 * | 5/2008 | Pai | F16M 11/04 248/157 |
| 2009/0236487 | A1 * | 9/2009 | Shi | A61B 6/0457 248/424 |
| 2009/0257561 | A1 * | 10/2009 | Okuno | A61B 6/4233 378/116 |
| 2010/0034346 | A1 * | 2/2010 | Kato | A61B 6/032 378/19 |
| 2011/0228456 | A1 * | 9/2011 | Tu | F16M 11/04 361/679.01 |
| 2012/0018596 | A1 * | 1/2012 | Valles Navarro | B66F 11/048 248/161 |
| 2013/0279662 | A1 * | 10/2013 | Kobayashi | A61B 6/4233 378/195 |

FOREIGN PATENT DOCUMENTS

| | | |
|---|---|---|
| JP | 2005-021233 | 1/2005 |
| JP | 2006-058124 | 3/2006 |
| JP | 3890163 | 3/2007 |
| JP | 2011-92612 | 5/2011 |
| JP | 2013-154146 | 8/2013 |

* cited by examiner

IMAGING STAND

The entire disclosure of Japanese Patent Application No. 2014-042286 filed on Mar. 5, 2014 including description, claims, drawings, and abstract are incorporated herein by reference in its entirety.

BACKGROUND OF THE INVENTION

1. Field of the Invention

The present invention relates to imaging stands, and more particularly, to an imaging stand to be used for imaging with a CR cassette or an FPD cassette installed therein.

2. Description of the Related Art

For the purpose of disease diagnoses and the like, radiation images such as X-ray images are widely used. Such radiation images for medical use are conventionally taken with the use of a screen-type film, but CR (Computed Radiography) devices using stimulable phosphor sheets have been developed to digitize radiation images. In recent years, radiographic imaging devices (flat panel detectors) that detect emitted radiation with radiation detecting elements and acquire the detected radiation as digital image data have been developed.

With a CR device, a CR cassette having a stimulable phosphor sheet in a cassette-type housing is conventionally installed in an imaging stand (also called a bucky imaging stand, a detector holder, or the like), and radiographic imaging is then performed in many cases. Radiographic imaging devices used to be developed as special-purpose devices formed integrally with supporting bases (see JP 3890163 B1 and JP 9-73144 A, for example). However, portable radiographic imaging devices that have radiation detecting elements and the like in housings and are designed to be portable have been developed and been put into practical use in recent years (see JP 2006-58124 A and JP 6-342099 A, for example). Such a portable radiographic imaging device will be hereinafter referred to simply as an FPD cassette. CR cassettes and FPD cassettes will be hereinafter collectively referred to as cassette-type detectors.

Meanwhile, various kinds of imaging stands each including a bucky into which a cassette-type detector is to be installed are being developed (see JP 2005-21233 A, for example). In many cases, an imaging stand is designed to be able to accommodate a cassette-type detector of 10×12 inches (quarter), 11×14 inches (large quarter), 14×14 inches (large square), 14×17 inches (half), 17×17 inches, or the like.

In a case where imaging is performed with a cassette-type detector of 14×17 inches installed in an imaging stand, for example, a cassette-type detector D is installed horizontally in an upper portion of the holder 102 in the bucky 101 of an imaging stand 100 as shown in FIG. 16A, or a cassette-type detector D is installed horizontally in a center position in terms of the vertical direction in the holder 102 as shown in FIG. 16B, or a cassette-type detector D is installed vertically in a center position in terms of the horizontal direction in the holder 102 as shown in FIG. 17A, for example.

Hereinafter, a case where a cassette-type detector D is installed horizontally in an upper portion of the holder 102 as shown in FIG. 16A will be referred to as "landscape top", a case where a cassette-type detector D is installed horizontally in a center position in terms of the vertical direction in the holder 102 as shown in FIG. 16B will be referred to as "landscape center", and a case where a cassette-type detector D is installed vertically in a center position in terms of the horizontal direction in the holder 102 as shown in FIG. 17A will be referred to as "portrait".

In a case where imaging is performed with a cassette-type detector D of 17×17 inches installed in an imaging stand, for example, the cassette-type detector D is installed in the holder 102 as shown in FIG. 17B. The position of the upper edge of a cassette-type detector D of 14×17 inches placed in the "landscape top" position (see FIG. 16A), the position of the upper edge of a cassette-type detector D of 14×17 inches placed in the "portrait" position (see FIG. 17A), and the position of the upper edge of a cassette-type detector D of 17×17 inches (see FIG. 17B) are made to be the same (at the same height from the floor surface or the like).

In a case where the orientation and the position of a cassette-type detector (an FPD cassette or a CR cassette) installed in a conventional imaging stand are changed, a complicated operation needs to be performed to pull the installed cassette-type detector D out of the holder 102 of the imaging stand 100, adjust the position of the guide 103 that is to hold the cassette-type detector D when the cassette-type detector D is installed, and insert the cassette-type detector D back into the holder 102.

As a result, not only the operability of the imaging stand 100 is degraded, but also the cassette-type detector D might be dropped when the cassette-type detector D is pulled out of or inserted back into the holder 102 as described above. If the cassette-type detector D is dropped, the cassette-type detector D might be broken, or the operator such as a radiological technologist might be injured as the cassette-type detector D falls onto a foot of the operator or crashes into the body of the operator, for example.

So as to improve such a situation and change the orientation and the like of the cassette-type detector D in the imaging stand 100 while avoiding ejection and insertion of the cassette-type detector D as much as possible, the holder 102 of the imaging stand 100 is provided on the back surface side of the imaging stand 100, and a rotating mechanism that can rotate the holder 102 relative to the supporting member 104 supporting the holder 102 from the back surface side has been developed and is attached to the imaging stand 100. In this structure, when the holder 102 holding a cassette-type detector D is rotated 90 degrees, the orientation and the position of the cassette-type detector D can be readily changed between the "landscape center" position (see FIG. 16B) and the "portrait" position (see FIG. 17A).

However, if the holder 102 is rotated 90 degrees while a cassette-type detector D is in the "landscape top" position (see FIG. 16A), the orientation of the cassette-type detector D is changed to a vertical orientation, but the cassette-type detector D is not placed at the center in terms of the horizontal direction in the holder 102 and is shifted to the right or left, as can be clearly seen when FIG. 16A is rotated 90 degrees clockwise or counterclockwise. Therefore, there is a need to provide not only the mechanism for rotating the holder 102 but also a mechanism for adjusting the position of the cassette-type detector D by moving the cassette-type detector D in the holder 102 or moving the holder 102. With the addition of such a mechanism, not only the operability of the imaging stand 100 is degraded, but also higher costs are required. Furthermore, if the mechanism becomes complicated, high-precision adjustment of the orientation and the position of the cassette-type detector D in the imaging stand 100 might become difficult.

SUMMARY OF THE INVENTION

The present invention has been made in view of the above problems, and an object thereof is to provide an imaging stand that can readily and accurately change the orientation and the position of the cassette-type detector held in a holder, without pulling out the cassette-type detector from the holder and pushing the cassette-type detector back into the holder, and can realize this feature at low costs.

To achieve the abovementioned object, according to an aspect, an imaging stand reflecting one aspect of the present invention comprises: a holder that holds an installed cassette-type detector; a supporting member that supports the holder from the back surface side; a circular gear secured to a shaft member protruding from the rotation center of the holder toward the supporting member on the back surface side, the holder being located in a different position from the position corresponding to the center of the radiation incidence surface of the cassette-type detector held in the holder; and a linear gear having concavities and convexities to be engaged with the teeth of the circular gear, the linear gear being attached to the supporting member, wherein, when the holder holding the cassette-type detector is rotated relative to the supporting member, the rotation center of the holder linearly moves relative to the supporting member as the holder rotates, and a change is caused in orientation and position of the cassette-type detector.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 1A is a perspective view, and FIG. 1B is a side view;

FIG. 12 is a diagram showing example structures of a slide plate, a stick-like member, and the like;

DESCRIPTION OF THE PREFERRED EMBODIMENTS

Hereinafter, an embodiment of an imaging stand of the present invention will be described with reference to the drawings. However, the scope of the invention is not limited to the illustrated examples.

Figure 1:
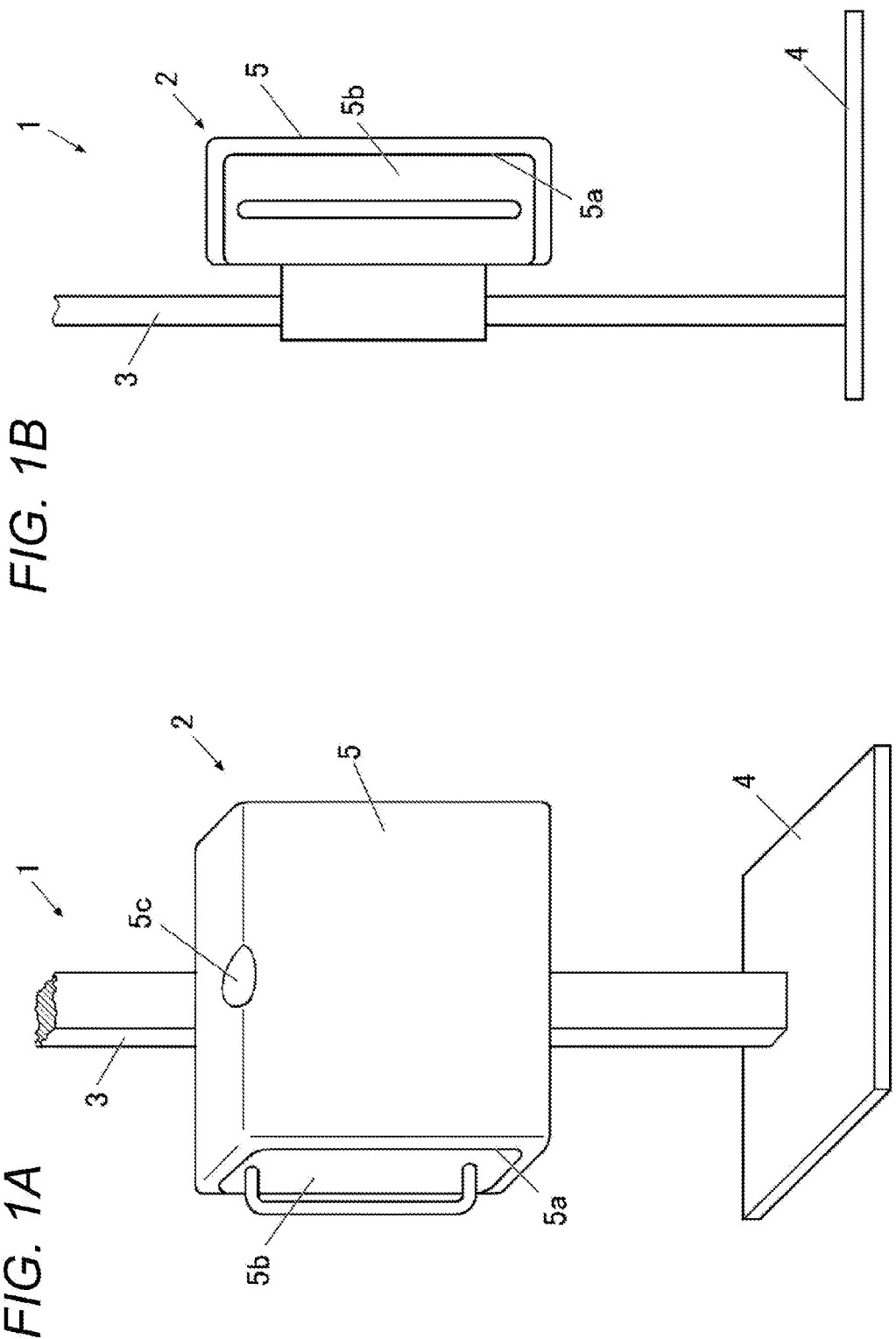
FIGS. 1A and 1B are diagrams showing the exterior of an imaging stand according to this embodiment.

FIGS. 1A and 1B are diagrams showing the exterior of an imaging stand according to this embodiment, FIG. 1A is a perspective view, and FIG. 1B is a side view. In this embodiment, the imaging stand 1 includes a bucky 2, a stand 3 that can lift up and down the bucky 2 while supporting the bucky 2, and a leg portion 4 for securing the stand 3 and the like to a floor surface or the like (not shown).

As shown in FIGS. 1A and 1B, in this embodiment, the imaging stand 1 is a so-called upright imaging stand, and imaging is performed while a patient as the subject stands (or is in an upright position) in front of the bucky 2. Although not shown in the drawings, the present invention can also be applied to a so-called recumbent imaging stand for performing imaging while a patient is lying (or in a recumbent position) on a top panel or the like.

In this embodiment, a cassette-type detector D may also be a CR cassette or an FPD cassette. In the description below, a cassette-type detector D mounted on the imaging stand 1 will be referred to simply as a panel D. That is, each panel D mentioned in the description below is a CR cassette or an FPD cassette. Further, in the description below, the side of the stand 3 of the imaging stand 1 (or the back side in FIG. 1A) will be referred to as the back surface side.

The bucky 2 includes a main unit 5 that accommodates an installed panel D (see FIG. 2 and other drawings described later). The main unit 5 is formed in a box-like shape that has an opening 5a in one of the right and left side surface portions. A door portion 5b is formed in the opening 5a, and the door portion 5b can open and close by virtue of a hinge mechanism (not shown) provided on the back surface side of the main unit 5. A panel D is installed and housed in the main unit 5 as described later, and the door portion 5b is closed, so that the opening 5a is blocked to enclose the panel D in the main unit 5. A recess 5c for the subject such as a patient to rest his/her chin thereon when roentgenographic imaging is performed on the chest of the subject is formed in the upper surface portion of the housing of the main unit 5.

Figure 2:
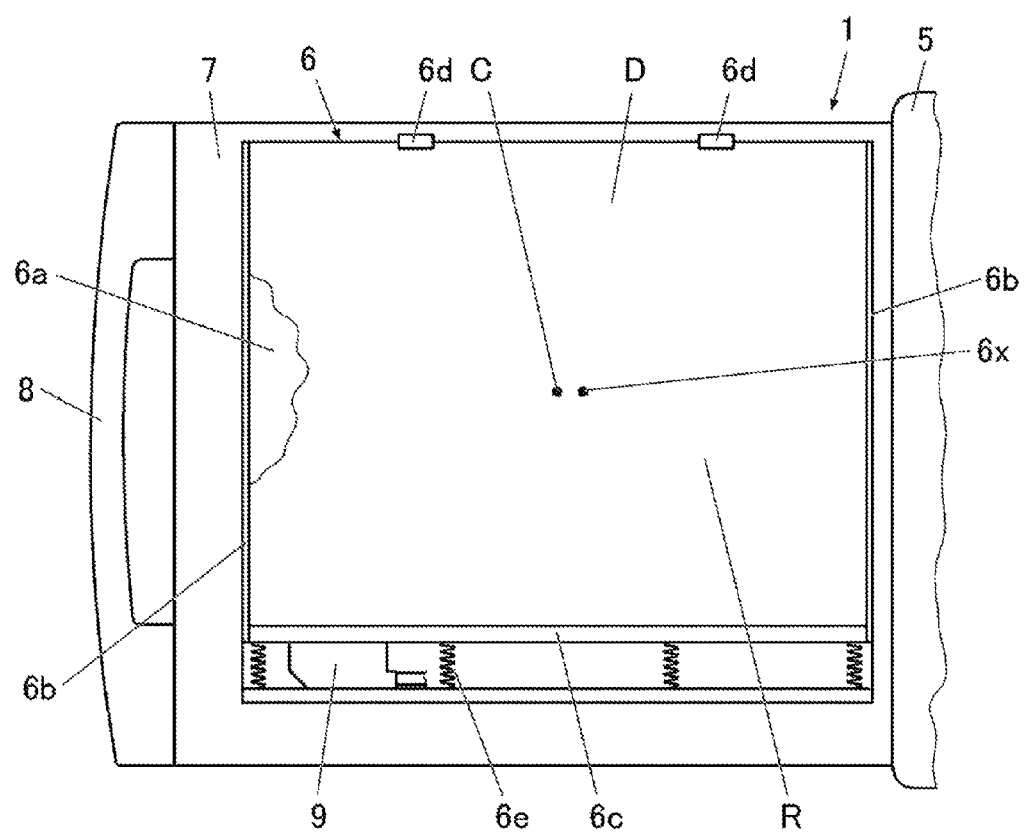
FIG. 2 is a diagram showing the structure and the like of the holder of the imaging stand in a situation where a panel of 14×17 inches is placed in a "landscape top" position.
Figure 16A:
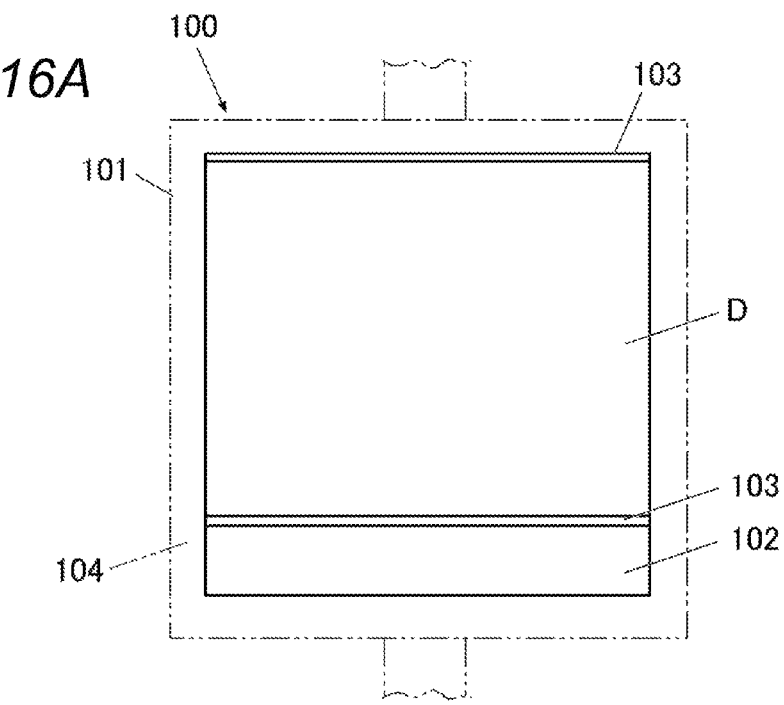
FIG. 16A is a diagram showing a situation where a cassette-type detector of 14×17 inches is installed in a "landscape top" position in a conventional imaging stand.

As shown in FIG. 2, the imaging stand 1 is designed so that a holder 6 that holds the installed panel D, a supporting member 7 that supports the holder 6 from the back surface side, and the like are housed in the main unit 5 of the bucky 2. When a handle 8 attached to the supporting member 7 is pulled forward, the holder 6, the supporting member 7, and the like are pulled out of the main unit 5, as shown in FIG. 2. When the handle 8 is pushed back, the holder 6, the supporting member 7, and the like are housed in the main unit 5, as shown in FIGS. 1A and 1B. FIG. 2 shows a case where the orientation and position of a panel D that is 14×17 inches in size and is installed in the holder 6 is "landscape top" (see FIG. 16A). Reference numeral 6x in FIG. 2 will be described later.

In this embodiment, the holder 6 includes: a back surface plate 6a that supports the installed panel D from the back surface side; two restricting plates 6b that are arranged perpendicularly to the back surface plate 6a, and restrict movement of the panel D in the horizontal direction in FIG. 2; a first locking claw 6c engaged with the lower edge portion of the panel D in FIG. 2; and two second locking claws 6d that are provided on the opposite side from the first locking claw 6c, and are engaged with the upper edge portion of the installed panel D in FIG. 2. The first locking claw 6c can slide up and down in FIG. 2, and is pushed toward the second locking claws 6d by springs 6e or the like.

So as to prevent the penal D installed in the holder 6 from protruding forward in FIG. 2, each of the first locking claw 6c and the second locking claws 6d is designed to have a rectangular shape minus a side in cross-section, and the first locking claw 6c and the second locking claws 6d are engaged with edge portions of the installed panel D on the side of a radiation incidence surface R. As shown in FIG. 2 and others, the first locking claw 6c can be designed as one elongated member. However, like the second locking claws 6d, the first locking claw 6c may be designed to be engaged with respective points of one edge portion of the panel D. Further, the second locking claws 6d have springs or the like (not shown), and are designed to move up and down in FIG. 2. The second locking claws 6d are pushed toward the first locking claw 6c by springs or the like. The structure of the portion in which the second locking claws 6d of the holder 6 are provided will be described later.

When a panel D is installed into the holder 6, the holder 6 is rotated 90 degrees in the counterclockwise direction in the situation of the holder 6 shown in FIG. 2 (the situation where no panel D is installed), and a panel D of 14×17 inches is then installed. Alternatively, the holder 6 is rotated 270 degrees in the counterclockwise direction in the situation shown in FIG. 2, and a panel D of 17×17 inches is then installed.

When a panel D of 14×17 inches is installed into the holder 6 from the side of the handle 8 (see FIG. 2) after the holder 6 is rotated 90 degrees in the counterclockwise direction in the situation shown in FIG. 2, for example, the right edge of the panel D is brought into contact with the first locking claw 6c of the holder 6 located on the opposite side from the handle 8, while vertical movement of the panel D is restricted by the restricting plates 6b located above and below of the holder 6 (to the right and the left of the holder 6 in FIG. 2). The first locking claw 6c is then temporarily moved to the right (or toward the main unit 5 of the bucky 2). In this situation, the left edge of the panel D is engaged with the second locking claws 6d. Accordingly, by virtue of the repulsive force of the springs 6e and other springs (not shown), the panel D is clamped between the first locking claw 6c and the second locking claws 6d. In this embodiment, when a panel D of 14×17 inches is installed into the holder 6 in the above manner, for example, the panel D is stably held by the holder 6.

When a panel D of 17×17 inches is installed into the holder 6 from the side of the handle 8 (see FIG. 2) after the holder 6 is rotated 270 degrees in the counterclockwise direction in the situation shown in FIG. 2, for example, the right edge of the panel D is brought into contact with the second locking claws 6d of the holder 6 located on the opposite side from the handle 8, while vertical movement of the panel D is restricted by the restricting plates 6b located above and below of the holder 6 (to the right and the left of the holder 6 in FIG. 2), as will be described later with reference to FIG. 6. The second locking claws 6d are then temporarily moved to the right (or toward the main unit 5 of the bucky 2). In this situation, the left edge of the panel D is engaged with the first locking claw 6c. Accordingly, by virtue of the repulsive force of the springs 6e and other springs (not shown), the panel D is clamped between the first locking claw 6c and the second locking claws 6d. In this embodiment, when a panel D of 17×17 inches is installed into the holder 6 in the above manner, for example, the panel D is also stably held by the holder 6.

When a panel D is pulled out of the holder 6, the panel D held by the holder 6 as described above is pressed against the locking claw(s) located to the right (or on the side of the main unit 5 of the bucky 2), and the locking claw(s) (the first locking claw 6c in the case of a panel D of 14×17 inches, and the second locking claws 6d in the case of a panel D of 17×17 inches) is moved to the right. In this manner, the lock on the panel D by the locking claw(s) located on the left side of the panel D (or on the side of the handle 8) is released. The panel D is then pulled toward the handle 8 in this situation, and is pulled out of the holder 6 with relative ease.

In a case where the installed panel D is an FPD cassette, a connector (not shown) is provided on a side surface of the panel D. However, where the first locking claw 6c is designed as one elongated member as shown in FIG. 2, an opening should be formed in the first locking claw 6c at the location corresponding to the location of the connector of the FPD cassette when the panel D is installed into the holder 6. With this arrangement, a connector 9 of the imaging stand 1 can be connected to the connector of the FPD cassette via the opening in a magnetic manner or the like.

A panel D is installed so that the radiation incidence surface R (or the surface from which radiation enters the panel D) is located on the front side in FIG. 2 (or the side on which the irradiation apparatus (not shown) that irradiates the panel D is located). C in FIG. 2 represents the center of the radiation incidence surface R of the panel D, but movement of the center C of the radiation incidence surface R of the panel D and the like will be described later.

In this embodiment, the imaging stand 1 is designed to be capable of rotating the holder 6 having a panel D installed therein relative to the supporting member 7 on the back surface side in a situation where the holder 6 and the supporting member 7 are pulled out of the main unit 5 as shown in FIG. 2. However, the structure and the like of the imaging stand 1 will be described later. Further, in this embodiment, the holder 6 is rotated 90 degrees at a time relative to the supporting member 7 in this situation, so that the orientation and the position of a panel D of 14×17 inches, for example, can be changed from "landscape top" (see FIG. 16A) to "portrait" (see FIG. 17A) to "landscape center" (see FIG. 16B). In the description below, this aspect of this embodiment is described.

In this embodiment, when the imaging stand 1 is actually used, a panel D of 14×17 inches is installed after the holder 6 not having any panel D installed therein is rotated 90 degrees in the counterclockwise direction in the situation shown in FIG. 2, and a panel D of 17×17 inches is installed after the holder 6 is rotated 270 degrees in the counterclockwise direction in the situation shown in FIG. 2. However, an explanation in accordance with this actual procedures will become complicated. Therefore, in the description below, the rotation angle in the situation shown in FIG. 2 is 0 degrees, and thereafter, the holder 6 is rotated 90 degrees at a time in the counterclockwise direction.

As will be described below, the orientation and the position of a panel D gradually change as the holder 6 is rotated 0 degrees, 90 degrees, 180 degrees, and 270 degrees in the counterclockwise direction. However, it is of course possible to rotate the holder 6 in the direction from 270 degrees to 180 degrees to 90 degrees to 0 degrees. As the holder 6 is rotated by each angle, the orientation and the position of a panel D can be changed to the orientation and the position corresponding to the angle.

Also, as can be seen from the description below, the present invention can be applied not only in cases where the panel D is 14×17 inches or 17×17 inches in size, but also in cases where the panel D is 11×14 inches or 14×14 inches in size. Thus, the present invention can be applied to panels D of various sizes.

[Principles of Change in the Orientation and the Position of a Panel D Only Through Rotation of the Holder]

As described above, in a case where the orientation and the position of a panel D installed and held in the holder 102 in the conventional imaging stand 100 are changed among "landscape top" (see FIG. 16A), "portrait" (see FIG. 17A), and "landscape center" (see FIG. 16B), there is the need to prepare a mechanism that not only rotates the holder 102 by 90 degrees at a time relative to the supporting member 104, but also moves the panel D in the holder 102 or moves the holder 102.

In the present invention, on the other hand, changes in the orientation and the position of a panel D installed and held in the holder 6 can be realized only through rotation of the holder 6 relative to the supporting member 7. In other words, according to the present invention, when a radiological technologist as the user rotates the holder 6 holding a panel D by 90 degrees at a time, the holder 6 automatically moves with the rotation, so that the orientation and the position of the panel D are adjusted to an appropriate orientation and an appropriate position. In the description below, the principles are described. The structure and the like for realizing the principles will be described later.

In the description below, the size of the panel D installed in the holder 6 is 14×17 inches. In this embodiment, through the above described rotating operation of the holder 6 relative to the supporting member 7, not only a panel D of 14×17 inches but also a panel D of 17×17 inches can be appropriately positioned, and therefore, this aspect is also described below.

In a situation where a panel D of 14×17 inches is installed in the holder 6, for example, and the rotation angle is 0 degrees as shown in FIG. 2, the panel D is placed in a "landscape top" position. When the holder 6 is rotated 90 degrees in the counterclockwise direction in that situation, for example, the panel D is put into a "portrait" state (see FIG. 17A). When the holder 6 is further rotated 90 degrees (180 degrees in total), the panel D is placed in a "landscape center" position. If a panel D of 17×17 inches is installed into the holder 6, for example, and the holder 6 is rotated 270 degrees in the counterclockwise direction, the panel D of 17×17 inches is appropriately placed as shown in FIG. 6, which will be described later.

Figure 16B:
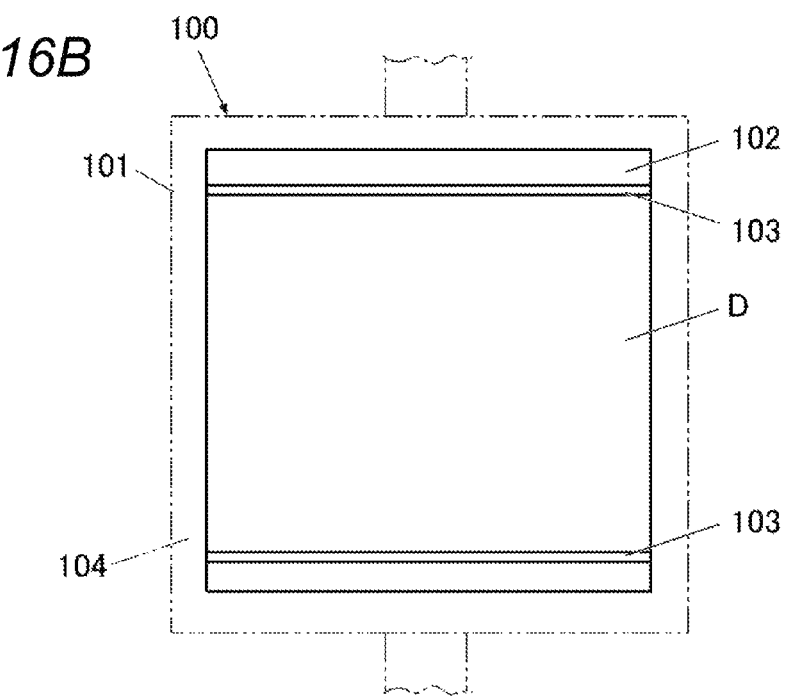
FIG. 16B is a diagram showing a situation where a cassette-type detector of 14×17 inches is installed in a "landscape center" position in a conventional imaging stand.
Figure 17A:
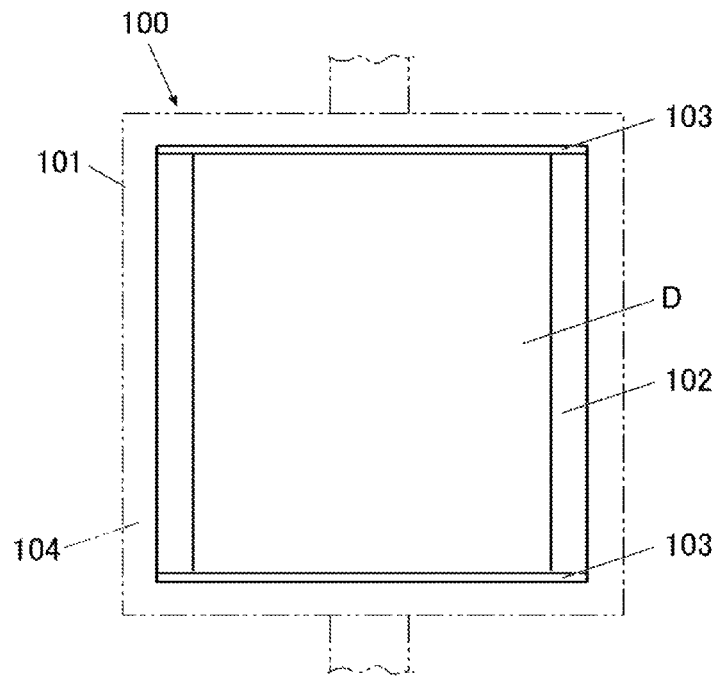
FIG. 17A is a diagram showing a situation where a cassette-type detector of 14×17 inches is installed in a "portrait" position in a conventional imaging stand.

First, attention is paid to the positions of the center C (see FIG. 2) of the radiation incidence surface R of a panel D of 14×17 inches in the respective cases where the orientation and the position of the panel D installed in the holder 6 are adjusted to the "landscape top" position (see FIG. 16A), where the holder 6 is rotated 90 degrees to place the panel D in the "portrait" position (see FIG. 17A), and where the holder 6 is further rotated 90 degrees to place the panel D in the "landscape center" position (see FIG. 16B). Hereinafter, the center C of the radiation incidence surface R of the panel D will be referred to simply as the center C of the panel D.

Figure 3A:
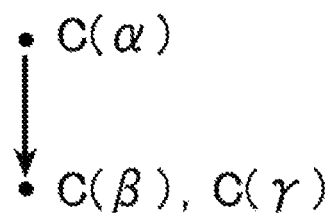
FIG. 3A is a diagram showing the trajectory of the center of the panel of 14×17 inches in a case where the holder is rotated.
Figure 3B:
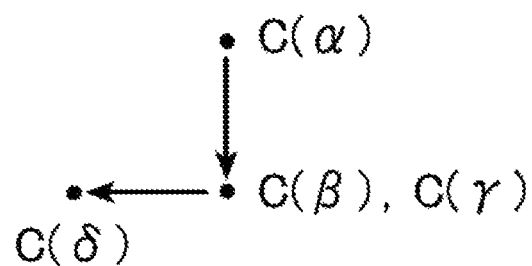
FIG. 3B is a diagram showing the trajectory of the point on the holder corresponding to the center of the panel of 14×17 inches in the case where the holder is rotated.

The position of the center C of the panel D in a case where the orientation and the position of the panel D of 14×17 inches installed in the holder 6 are "landscape top" (see FIG. 16A) is the position α shown in FIG. 3A, for example. FIG. 3A and FIG. 3B, which will be described later, are enlarged views showing movement of the center C (or the later described point C on the holder 6 corresponding to the center C) of a panel D when the panel D installed in the holder 6 is seen as shown in FIG. 2.

Figure 4:
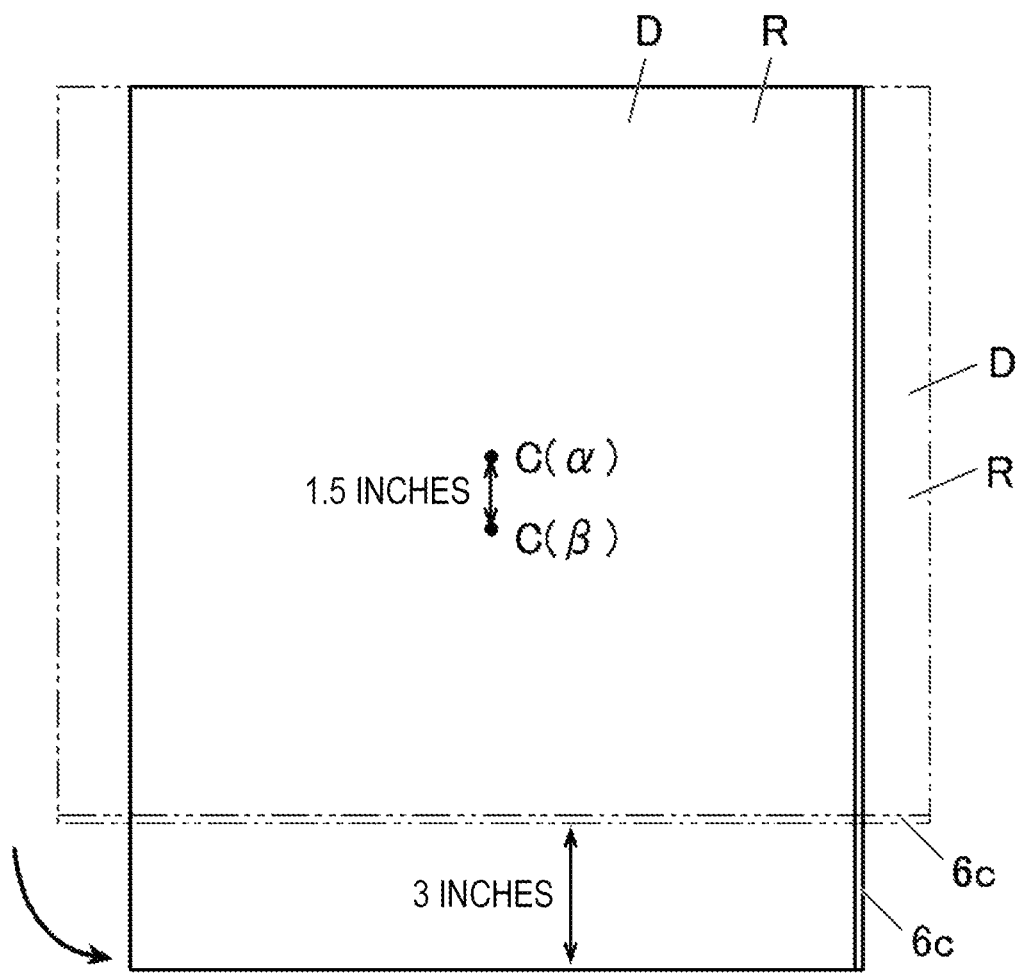
FIG. 4 is a diagram for explaining that, when the holder is rotated 90 degrees, the orientation and the position of the panel of 14×17 inches change from "landscape top" to "portrait", and the center of the panel of 14×17 inches moves.

When the panel D of 14×17 inches and the holder 6 are rotated 90 degrees in the counterclockwise direction (so that the upper side of the panel D shown in FIG. 2 becomes the left side), and is placed in the "portrait" position (see FIG. 17A), the vertical panel D is not moved to the left but is located at the center in terms of the horizontal direction as shown in FIG. 4. As described above, the position of the upper edge of the panel D of 14×17 inches set in the "landscape top" position is the same as the position (or the height from the floor surface or the like) of the upper edge of the panel D set in the "portrait" position (see FIG. 4). Accordingly, the center C of the panel D placed in the "portrait" position is in the position β located immediately below the position α, as shown in FIG. 3A.

In other words, so as to realize changes in the orientation and the position of the panel D installed and held in the holder 6 only through rotation of the holder 6 relative to the supporting member 7 as described above, the position of the center C of the panel D placed in the "portrait" position automatically moves (with the above rotation) to the position β immediately below the position α in FIG. 3A, while the panel D in the "landscape top" position shown in FIG. 4 and the holder 6 (not shown in FIG. 4) are rotated 90 degrees in the counterclockwise direction. In this case, the position of the center C of the panel D moves 1.5 inches (=(17−14)/2) from the position α to the position β immediately below the position α in FIG. 3A, as can be seen from FIG. 4.

Figure 5:
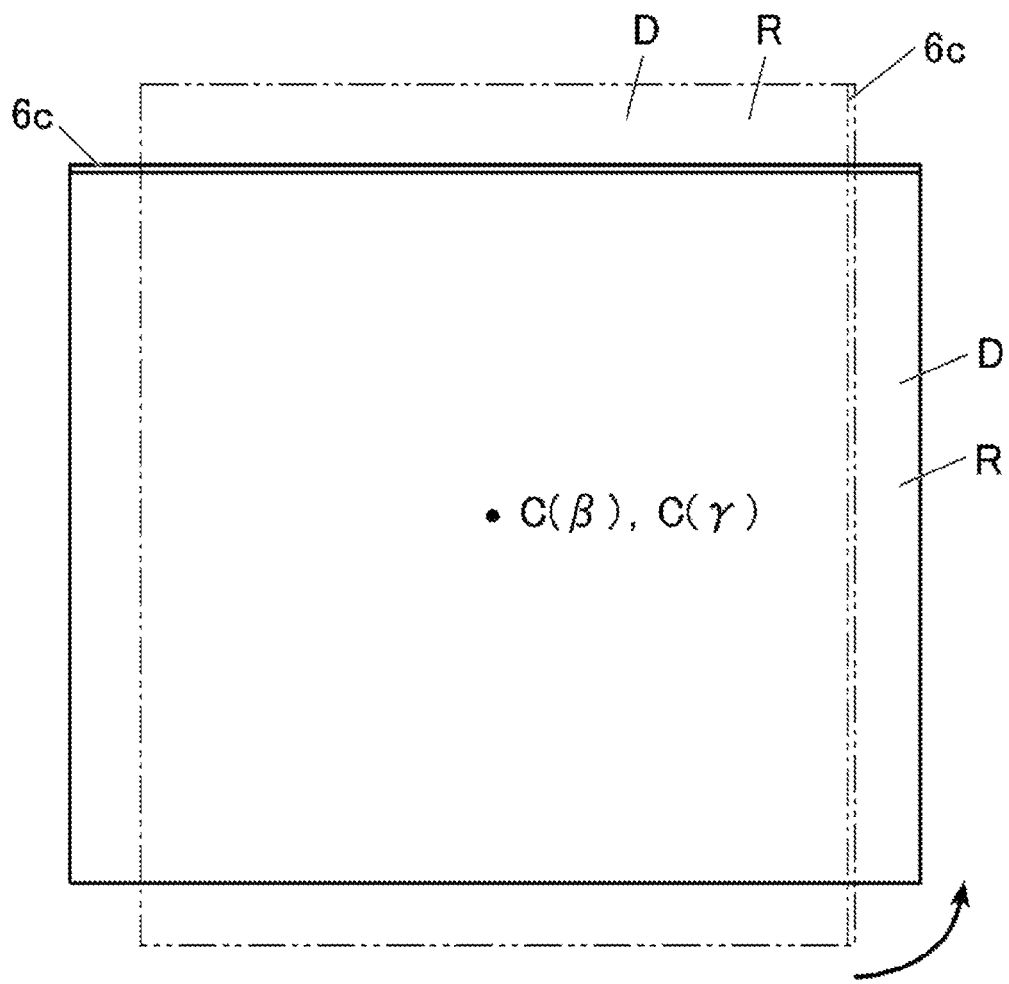
FIG. 5 is a diagram for explaining that, when the holder is further rotated 90 degrees, the orientation and the position of the panel of 14×17 inches change from "portrait" to "landscape center", and the center of the panel of 14×17 inches does not move.

When the panel D of 14×17 inches and the holder 6 are further rotated 90 degrees in the counterclockwise direction, and is placed in the "landscape center" position (see FIG. 16B), the position β of the center C of the panel D in the "portrait" position is the same as the position γ of the center C of the panel D in the "landscape center" position, as shown in FIG. 3A. That is, the center C of the panel D does not move, and the panel D rotates 90 degrees in the counterclockwise direction about the same positions β and γ, as shown in FIG. 5

Therefore, in a case where the panels D to be installed into the holder 6 are only of the 14×17 inch type (or a 10×12 inch type or a 11×14 inch type, for example), the center C of the panel D moves as shown in FIG. 3A every time the panel D of 14×17 inches and the holder 6 are rotated 90 degrees in the counterclockwise direction, so as to change the orientation and the position of the panel D from "landscape top" to "portrait" to "landscape center".

The panel D is rotated while being held in the holder 6. Therefore, so as to move the center C of the panel D as shown in FIG. 3A, the holder 6 is rotated relative to the supporting member 7 so that the point (hereinafter referred to as the point C) on the holder 6 corresponding to the center C of the panel D moves from C(α) to C(β) to C(γ) shown in FIG. 3A as the holder 6 is rotated 90 degrees at a time in the counterclockwise direction, while the center C of the panel D is allowed to automatically move.

In this embodiment, not only a panel D of 14×17 inches but also a panel D of 17×17 inches can be appropriately positioned through rotating operation of the holder 6 relative to the supporting member 7 as described above. In this embodiment, when the holder 6 is rotated 270 degrees in the counterclockwise direction from a zero degrees state, and a panel D of 17×17 inches is installed into the holder 6 in that situation as described above, the panel D of 17×17 inches is placed in an appropriate position as shown in FIG. 6. The "panel D of 17×17 inches being placed in an appropriate position" means that, when the holder 6 having a panel D of 17×17 inches installed therein is housed in the main unit 5 of the bucky 2 (see FIGS. 1A and 1B), the panel D of 17×17 inches is placed in an appropriate position in the main unit 5, without shifting in the vertical direction or the horizontal direction.

Figure 6:
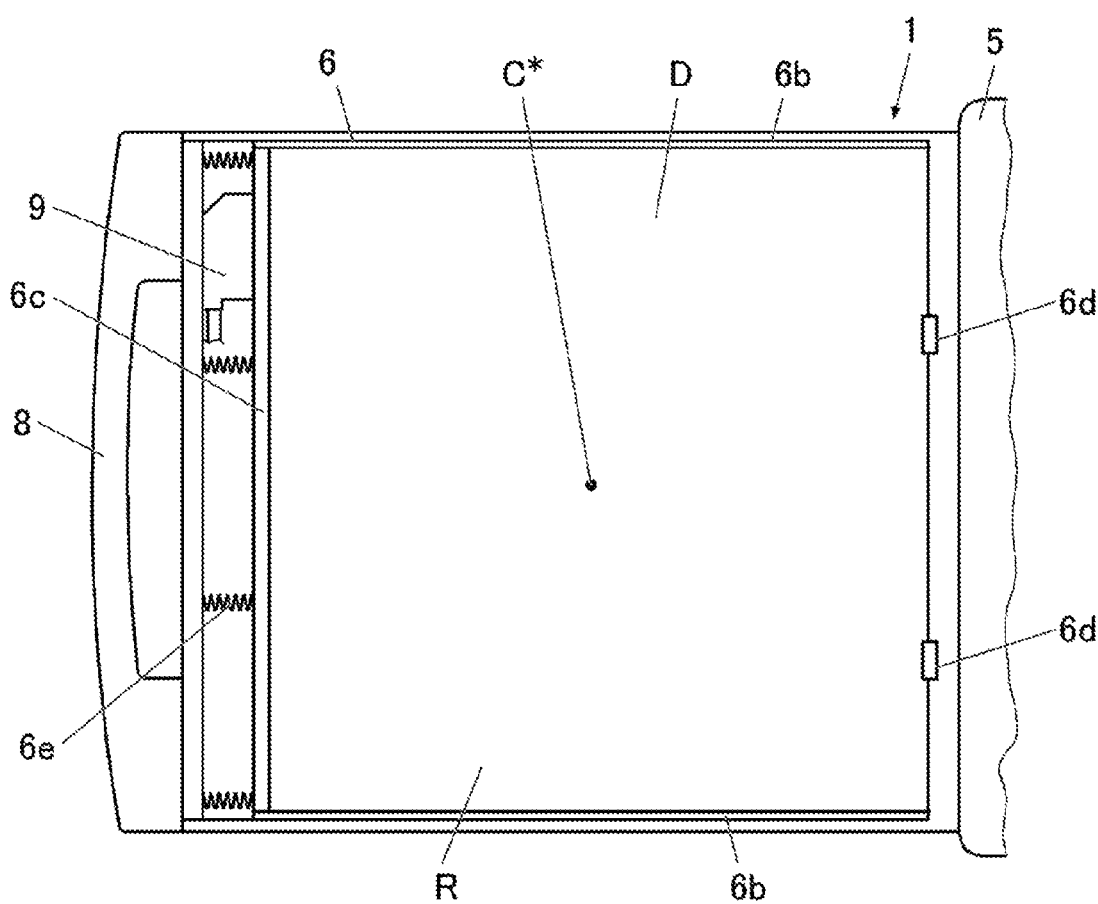
FIG. 6 is a diagram showing a situation where a panel of 17×17 inches is installed after the holder is rotated 270 degrees.
Figure 7:
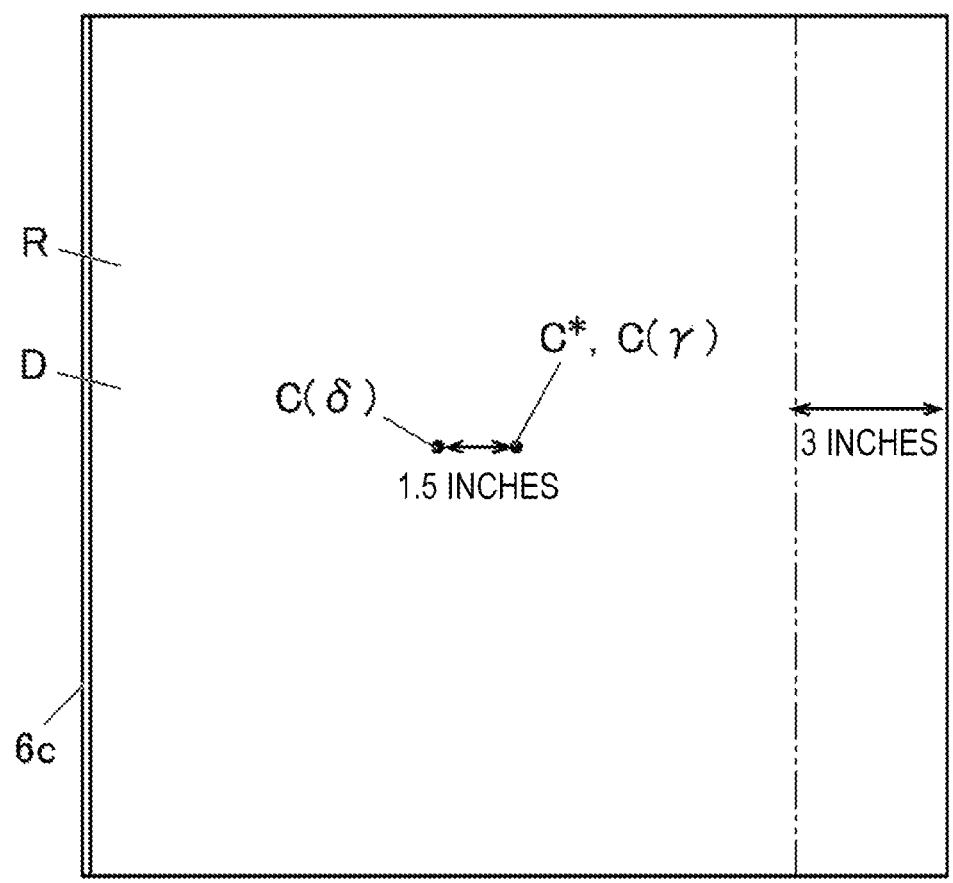
FIG. 7 is a diagram showing the positions of a panel of 17×17 inches and a panel of 14×17 inches, and the positions of the centers of the respective panels, after the holder is rotated 270 degrees.

In a case where a panel D of 17×17 inches is in an appropriate position as shown in FIG. 6, the position of the center C* of the radiation incidence surface of the panel D of 17×17 inches (see FIG. 6; the center C will be hereinafter referred to as the center C* of the panel D) should be the same as the position of the center C of a panel D of 14×17 inches in the above described case where the panel D of 14×17 inches is placed in the "portrait" orientation and position, or the above described center C(γ) (see FIG. 5 and others), as shown in FIG. 7. This is because the length of the panel D of 14×17 inches placed in the "portrait" position is 17 inches in the vertical direction, which is the same as the length of the panel D of 17×17 inches. Therefore, the center of the panel D of 14×17 inches placed in the "portrait" position is in the same position as the center of the panel D of 17×17 inches in the vertical direction. Furthermore, as the panel D of 14×17 inches placed in the "portrait" position is located at the center in terms of the horizontal direction, the center of the panel D of 14×17 inches placed in the "portrait" position is also in the same position as the center of the panel D of 17×17 inches in the horizontal direction.

Meanwhile, where C(δ) represents the center C of the panel D of 14×17 inches in a case where the panel D of 14×17 inches, instead of the panel D of 17×17 inches, is installed in the holder 6 shown in FIG. 6 or the holder 6 rotated 270 degrees in the counterclockwise direction, as shown in FIG. 7, the position of the center C(δ) of the panel D of 14×17 inches virtually installed in the holder 6 is 1.5 inches to the left of the position of the center C* of the panel D of 17×17 inches installed in the holder 6 in this situation where the holder 6 has been rotated 270 degrees in the counterclockwise direction as shown in FIGS. 6 and 7.

That is, in a case where the center C of the panel D of 14×17 inches is regarded as a position on the holder 6, when the holder 6 is rotated 0 degrees, 90 degrees, and then 180 degrees in the counterclockwise direction, the point C on the holder 6 moves from C(α) to C(β) to C(γ) as shown in FIG. 3A. However, so as to put the holder 6 into a state where the holder 6 is further rotated 90 degrees in the counterclockwise direction after rotated 180 degrees, or a state where the holder 6 is rotated 270 degrees as shown in FIGS. 6 and 7 (a state where the panel D of 17×17 inches is placed in an appropriate position), the holder 6 should be moved while being rotated so that the point C moves to the position of the point C(δ) that is located 1.5 inches to the left of the point C(γ) as shown in FIG. 3B.

[Structure and the Like Unique to the Present Invention]

Next, the structure and the like for moving the holder 6 of the imaging stand 1 in the above manner are described. The actions of the imaging stand 1 according to this embodiment are now described as well.

In this embodiment, the holder 6 has the rotation center in a position that is not the position of the point C on the holder 6 corresponding to the center C of the panel D held in the holder 6. When the holder 6 holding the panel D is rotated 90 degrees at a time in the counterclockwise direction relative to the supporting member 7, the rotation center of the holder 6 linearly moves relative to the supporting member 7 as the holder 6 rotates, and a change is caused in the orientation and the position of the panel D. This aspect is described below in detail.

Figure 8:
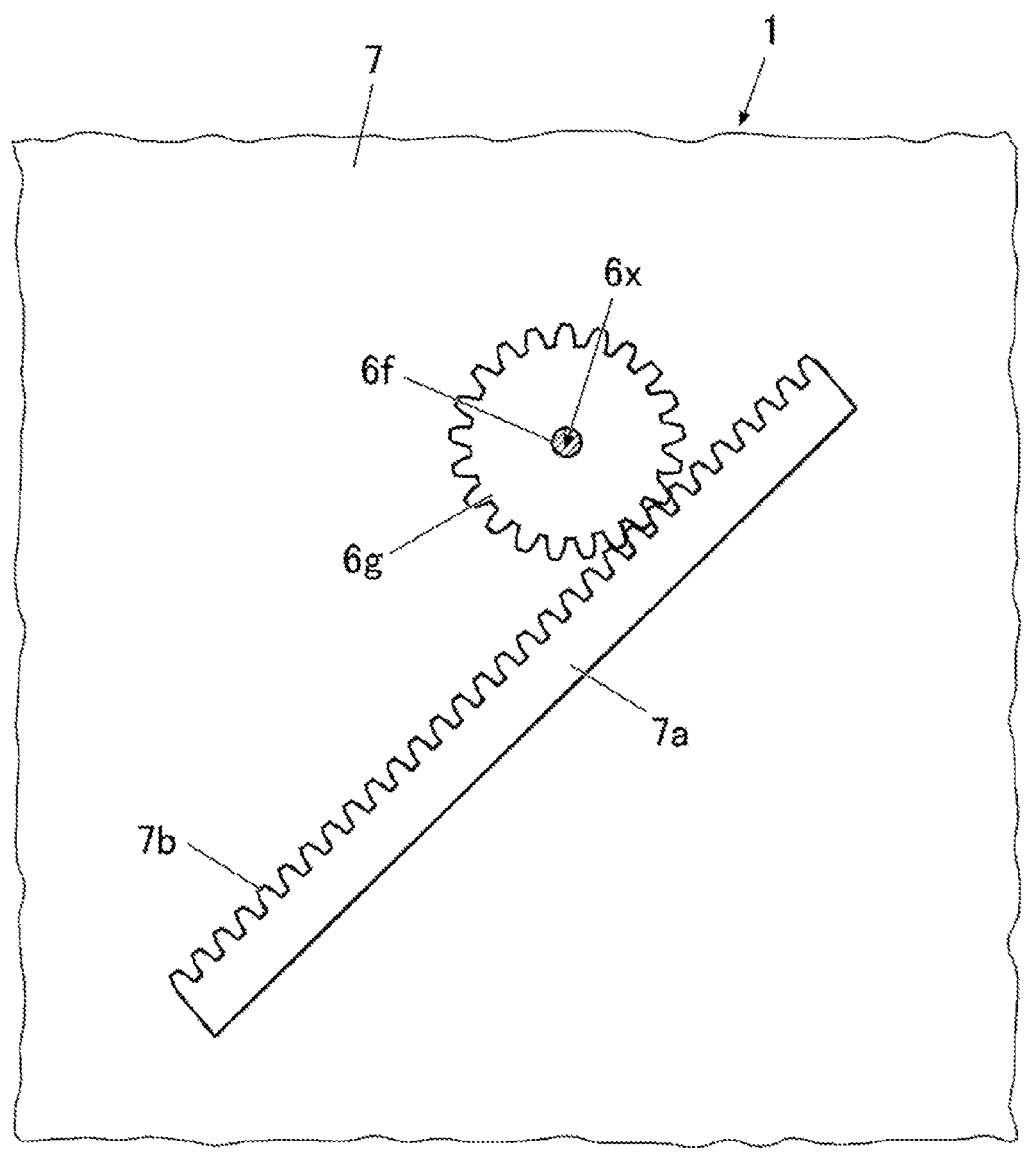
FIG. 8 is a diagram showing the structures of a circular gear, the supporting member, and the like in this embodiment.

As shown in FIG. 8, a linear gear 7a having concavities and convexities in an engaging portion 7b on the upper side is formed in the supporting member 7. The linear gear 7a is tilted at 45 degrees with respect to a horizontal surface.

A shaft member 6f is integrally formed with the holder 6 so that the shaft member 6f protrudes from the position of the rotation center 6x of the holder 6 (not shown) placed on the front side in FIG. 8 toward the supporting member 7 on the back surface side. The shaft member 6f rotates about the rotation center 6x as the holder 6 rotates in the above described manner. A circular gear 6g is secured to the shaft member 6f, and the teeth of the circular gear 6g are to be engaged with the concavities and convexities of the engaging portion 7b of the linear gear 7a (or the teeth of the linear gear 7a).

Figure 14:
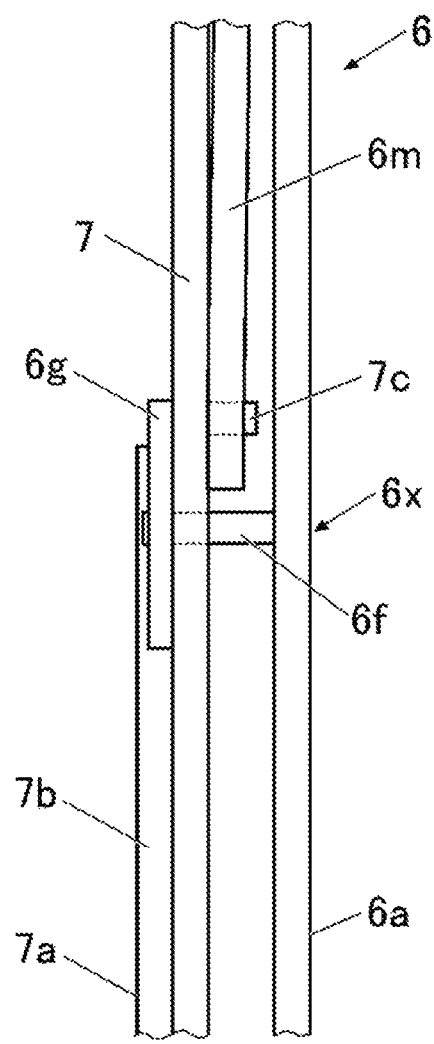
FIG. 14 is a side view of the holder 6 at the rotation angle of 0 degrees and others, seen from the left side in FIG. 13.

In this embodiment, as shown in FIG. 14, which will be described later, the linear gear 7a is provided on the surface on the opposite side of the supporting member 7 from the side on which the holder 6 and the like are provided, and an elongated opening (not shown in FIG. 14) formed at an upper portion of the linear gear 7a of the supporting member 7 and extends parallel to the engaging portion 7b of the linear gear 7a. The shaft member 6f formed to protrude from the holder 6 toward the supporting member 7 is inserted into this opening, and the circular gear 6g formed at the top edge of the shaft member 6f is engaged with the linear gear 7a. That is, when seen from the side of the holder 6, the circular gear 6g and the linear gear 7a are engaged with each other on the back surface side of the supporting member 7. As will be described later, when the circular gear 6g moves along the linear gear 7a (see FIGS. 9A and 9B, and FIGS. 10A and 10B, which will be described later), the shaft member 6f moves in the elongated opening (not shown). Therefore, the elongated opening is tilted 45 degrees with respect to a horizontal surface, so as to match the tilting of the engaging portion 7b of the linear gear 7a. Alternatively, the linear gear 7a, the circular gear 6g, and the like may be provided on the surface of the supporting member 7 on the side having the holder 6 and the like provided thereon.

In the above described structure in this embodiment, the holder 6 of the imaging stand 1 is moved while being rotated 90 degrees at a time in the counterclockwise direction as described above, so that the orientation and the position of a panel D of 14×17 inches can be changed from "landscape top" to "portrait" to "landscape center". Also, a panel D of 17×17 inches is inserted into the holder 6 after the holder 6 is rotated 270 degrees in the counterclockwise direction, so that the panel D of 17×17 inches can be placed in an appropriate position as shown in FIG. 6.

This aspect is described below in detail. In the drawings to be described below, the circular gear 6g is represented by a circle, and the engaging portion 7b having the concavities and convexities of the linear gear 7a is represented by a straight line for simplification.

Figure 9A:
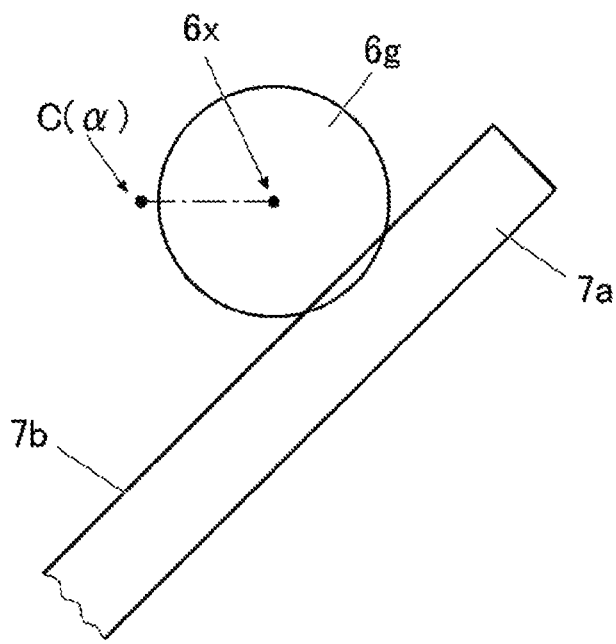
FIG. 9A is a diagram showing the positions and the like of the circular gear and the center of a panel of 14×17 inches in a case where the rotation angle of the holder is 0 degrees.

First, in a situation where the rotation angle of the holder 6 is 0 degrees, the circular gear 6g is located at an upper portion of the linear gear 7a, as shown in FIG. 9A. In a perspective view of a panel D of 14×17 inches installed in the holder 6 like FIG. 2, the circular gear 6g is located in such a position that the center C of the panel D (or the corresponding point C on the holder 6, which is C(α) in FIG. 3B and others) is located to the left of the rotation center 6x of the holder 6 or at the left edge of the circular gear 6g, as shown in FIG. 9A.

Figure 9B:
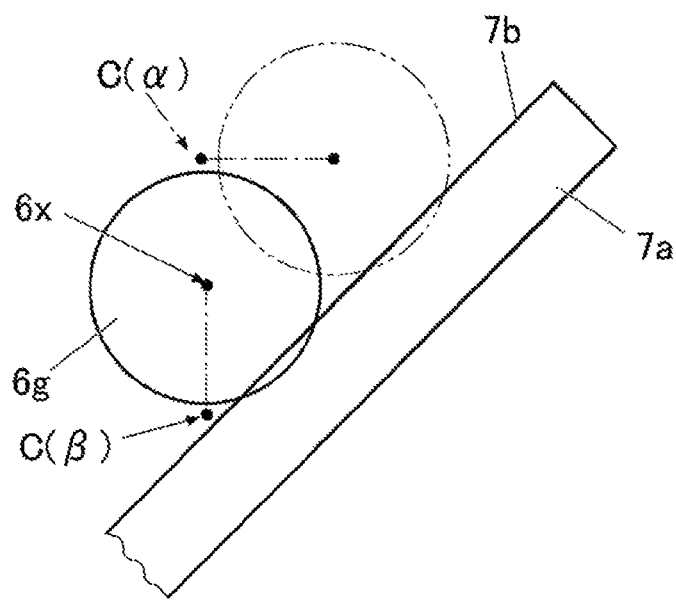
FIG. 9B is a diagram showing the positions and the like of the circular gear and the center of the panel of 14×17 inches after the holder is rotated 90 degrees.

When the holder 6 is rotated 90 degrees in the counterclockwise direction in this situation, the circular gear 6g also rotates 90 degrees in the counterclockwise direction, and moves obliquely downward along the engaging portion 7b of the linear gear 7a, as shown in FIG. 9B. At this point, the holder 6 not shown in FIG. 9B rotates 90 degrees in the counterclockwise direction about the rotation center 6x as the circular gear 6g rotates. Accordingly, the center C of the panel D of 14×17 inches installed in the holder 6 moves from the position on the left side of the rotation center 6x shown in FIG. 9A to a position immediately below the rotation center 6x, as shown in FIG. 9B.

As the holder 6 is rotated 90 degrees in the counterclockwise direction, the center C of the panel D of 14×17 inches moves from the position α to the position β located immediately below the position α, as shown in FIG. 9B. As the holder 6 having the panel D of 14×17 inches installed therein is simply rotated 90 degrees in the counterclockwise direction in the above manner, the 1.5-inch movement of the center C from the position α to the position β shown in FIG. 3B is realized, and the change in the orientation and the position of the panel D of 14×17 inches from "landscape top" to "portrait" shown in FIG. 4 is realized.

Figure 10A:
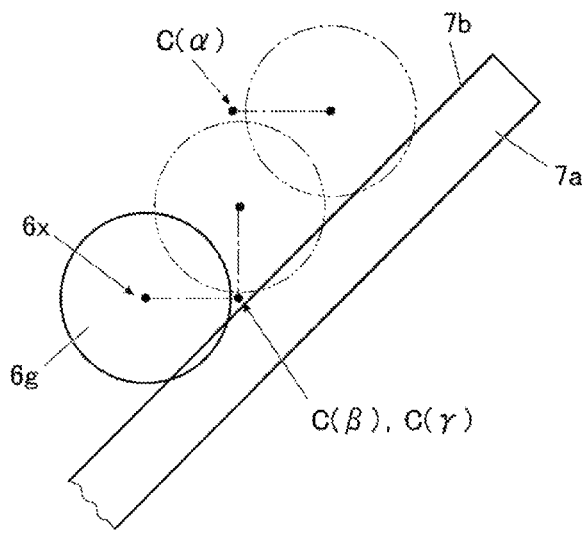
FIG. 10A is a diagram showing the positions and the like of the circular gear and the center of a panel of 14×17 inches after the holder is rotated 180 degrees.

When the holder 6 having the panel D of 14×17 inches installed therein is further rotated 90 degrees in the counterclockwise direction, the circular gear 6g further rotates 90 degrees in the counterclockwise direction, and moves obliquely downward along the engaging portion 7b of the linear gear 7a, as shown in FIG. 10A. As the holder 6 not shown in FIG. 10A also rotates 90 degrees in the counterclockwise direction about the rotation center 6x with the rotation of the circular gear 6g, the center C of the panel D of 14×17 inches installed in the holder 6 moves from the position immediately below the rotation center 6x shown in FIG. 9B to a position to the right of the rotation center 6x, as shown in FIG. 10A.

As the holder 6 is further rotated 90 degrees in the counterclockwise direction, the center C of the panel D of 14×17 inches moves from the position β but eventually returns to the position β, as shown in FIG. 10A (see C(γ) in FIG. 10A). In the above manner, an operation can be performed so that the position β of the center C at the time when the holder 6 having the panel D of 14×17 inches installed herein is rotated 90 degrees in the counterclockwise direction is the same as the position γ of the center C at the time when the holder 6 is further rotated 90 degrees (180 degrees in total) in the counterclockwise direction as shown in FIG. 3B, and the change in the orientation and the position of the panel D of 14×17 inches from "portrait" to "landscape center" shown in FIG. 5 is realized.

Figure 10B:
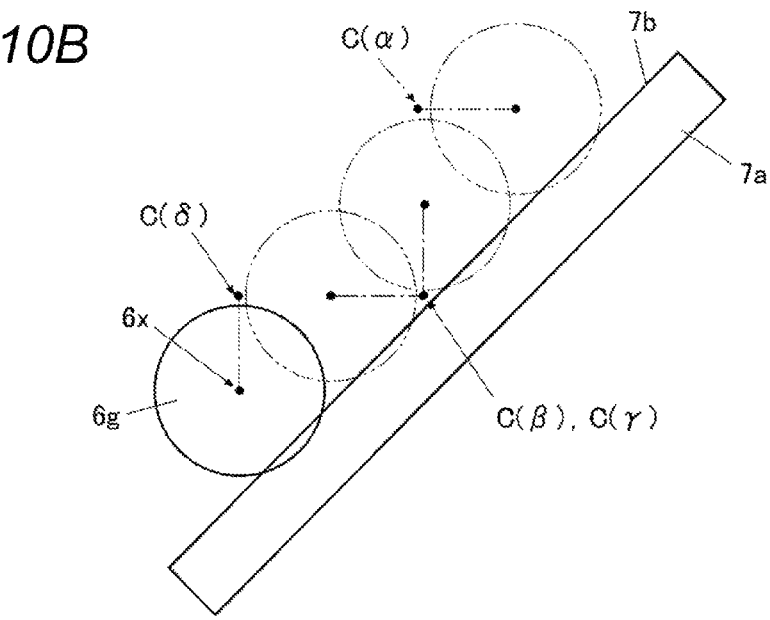
FIG. 10B is a diagram showing the positions and the like of the circular gear and the center of the panel of 14×17 inches after the holder is rotated 270 degrees.

When the holder 6 is further rotated 90 degrees (270 degrees in total) in the counterclockwise direction in the situation where the holder 6 has already been rotated 180 degrees in total in the counterclockwise direction, the circular gear 6g further rotates 90 degrees in the counterclockwise direction, and moves obliquely downward along the engaging portion 7b of the linear gear 7a, as shown in FIG. 10B. Accordingly, the point C corresponding to the center C of the panel D in the case where the panel D of 14×17 inches is installed in the holder 6 moves from the position on the right side of the rotation center 6x shown in FIG. 10A to the position δ immediately above the rotation center 6x, as shown in FIG. 10B.

That is, when the holder 6 already rotated 180 degrees in the counterclockwise direction is further rotated 90 degrees in the counterclockwise direction, the position of the center C of the panel D in the case where the panel D of 14×17 inches is installed in the holder 6 moves 1.5 inches leftward to the position δ from the position γ in FIG. 10B.

When a panel D of 17×17 inches is installed into the holder 6 in this situation, the state shown in FIG. 6 is realized, and the position of the center C* of the panel D of 17×17 inches is 1.5 inches to the right of the position δ of the center C of the panel D in the case where the panel D of 14×17 inches is installed in the holder 6, as shown in FIG. 7. Accordingly, the position of the center C* of the panel D of 17×17 inches installed in the holder 6 is the same as the positions β and γ of the center C in the case where the panel D of 14×17 inches is placed in the "portrait" position and the "landscape center" position, and the panel D of 17×17 inches is eventually placed in the appropriate position shown in FIG. 6.

As described above, as the panel D of 17×17 inches is installed after the holder 6 is rotated 270 degrees in the counterclockwise direction, the center C* of the panel D of 17×17 inches can be located in the center position (the same position as the positions β and γ of the center C in the case where the panel D of 14×17 inches is placed in the "portrait" position and the "landscape center" position) as shown in FIG. 6, and the panel D of 17×17 can be placed in the appropriate position.

With the above described structure, the circular gear 6g is moved, while being rotated, along the engaging portion 7b on the upper side of the linear gear 7a tilted 45 degrees with respect to a horizontal surface in this embodiment. Accordingly, the circular gear 6g can be linearly moved with precision, and the circular gear 6g can be moved while being rotated, with the movement of the circular gear 6g being in accurate synchronization with the rotation (or the rotation angle).

Accordingly, as the holder 6 holding a panel D is rotated 90 degrees at a time in the counterclockwise direction as described above, the orientation and the position of a panel D of 14×17 inches can be changed among "landscape top", "portrait", and "landscape center". Also, as a panel D of 17×17 inches is installed into the holder 6 after the holder 6 is rotated 270 degrees in the counterclockwise direction, the positioning of the panel D of 17×17 inches can be performed with high precision. Furthermore, a radiological technologist or the like simply has to rotate the holder 6 holding a panel D. Accordingly, the panel D does not need to be pulled out of and be pushed back into the holder 6, and the orientation and the position of the panel D can be very easily changed.

Also, in this embodiment, the above described operation of the holder 6 can be realized simply with the use of the circular gear 6g, the linear gear 7a, and the like. Accordingly, increases in the production cost of the imaging stand 1 can be prevented. Also, a radiological technologist or the like simply has to manually rotate the holder 6 holding a panel D, and there is no need to use an electric device such as a motor at least for rotating the holder 6. The imaging stand 1 according to this embodiment can also realize the above described operation at low costs in that aspect.

The circular gear 6g has such a diameter as to realize the above described operation (particularly, the operation illustrated in FIG. 3B). As can be seen from FIG. 10B, for example, the diameter of the circular gear 6g is slightly shorter than the distance between the point C(α) and the point C(β), and, as can be calculated, the diameter of the circular gear 6g is approximately 1.35 inches in a case where the distance between the point C(α) and the point C(β) is 1.5 inches as described above.

The "1.5 inches" is calculated by dividing the difference between 17 inches and 14 inches, which are the length of the long side and the length of the short side of the panel D of 14×17 inches, by 2 ((the length of the long side−the length of the short side)/2). Therefore, where the imaging stand 1 is of a type that performs imaging with a panel D of 11×14 inches or 14×14 inches being installed, "(the length of the long side−the length of the short side)/2" is 1.5 inches, and the circular gear 6g is designed to have the same size as the circular gear 6g of this embodiment. Where the imaging stand 1 is of a type that performs imaging with a panel D of 10×12 inches being installed, "(the length of the long side−the length of the short side)/2" is 1 inch, and the circular gear 6g is designed to have a size that is two thirds of the size of the circular gear 6g of this embodiment.

[Effects]

As described above, in the imaging stand 1 according to this embodiment, the holder 6 has the rotation center 6x in a different position from the position C corresponding to the center C of the radiation incidence surface R of the panel D or a cassette-type detector D (an FPD cassette or a CR cassette) held in the holder 6. When the holder 6 holding the cassette-type detector D is rotated relative to the supporting member 7, the rotation center 6x of the holder 6 linearly moves relative to the supporting member 7 as the holder 6 rotates, and a change is caused in the orientation and the position of the cassette-type detector D.

With this structure, the orientation and the position of the cassette-type detector D held in the holder 6 can be appropriately and precisely changed among "landscape top", "portrait", and "landscape center". Accordingly, a change and the like can be caused in the orientation and the position of the cassette-type detector D simply by rotating the holder 6 holding the cassette-type detector D, without pulling the holder 6 out of the cassette-type detector D and pushing the holder 6 back into the cassette-type detector D. With the same rotating operation of the holder 6, a cassette-type detector D of some other size (17×17 inches in the above described example) can also be positioned with high precision. Furthermore, where these actions are realized with the use of the circular gear 6g and the like, the above described high-precision operation can be realized at low costs.

Therefore, when the orientation and the position of a cassette-type detector D are changed or adjusted, there is no need to pull out the cassette-type detector D from the holder of the imaging stand, adjust the position of the guide, and insert the cassette-type detector D back into the holder as in a conventional imaging stand. Accordingly, the operability of the imaging stand 1 is higher. During the above described operation, a cassette-type detector D might be dropped and be broken, or a radiological technologist or the light might bump into a cassette-type detector D and be injured. With the imaging stand 1, such accidents can be appropriately prevented.

In this embodiment, the holder 6 holding a cassette-type detector D is rotated in the counterclockwise direction.

However, the holder 6 may be rotated in the clockwise direction. In that case, the linear gear 7a is not tilted to the right as shown in FIG. 8 and other drawings, but needs to be tilted to the left, for example, though not shown in the drawings.

In view of general circular motion, rotating the holder 6 by 270 degrees in the counterclockwise direction from the position of the holder 6 shown in FIG. 2 is equal to rotating the holder 6 by 90 degrees in the clockwise direction from the position of the holder 6 shown in FIG. 2, for example. As can be seen from the movement of the circular gear 6g relative to the linear gear 7a shown in FIGS. 9A to 10B, however, if the holder 6 is not rotated 270 degrees in the counterclockwise direction as described above but is rotated 90 degrees in the clockwise direction when a cassette-type detector D of 17×17 inches is positioned, for example, the circular gear 6g might move to the upper right and be disengaged from the linear gear 7a. Even if the circular gear 6g is not disengaged from the linear gear 7a, the center C* of the radiation incidence surface R of the cassette-type detector D of 17×17 inches is not placed in an appropriate position after the holder 6 is rotated 90 degrees in the clockwise direction. As a result, the cassette-type detector D of 17×17 inches cannot be placed in an appropriate position.

In a case where the above described operation (see FIG. 3B) of the holder 6 is realized with the use of the circular gear 6g, the linear gear 7a, and the like as in the above described embodiment, when a cassette-type detector D of 17×17 inches is positioned, the holder 6 needs to be rotated not 90 degrees in the clockwise direction but 270 degrees in the counterclockwise direction (or the holder 6 needs to be rotated not 90 degrees in the counterclockwise direction but 270 degrees in the clockwise direction in a case where the linear gear 7a is tilted in the opposite direction and the holder 6 is rotated in the clockwise direction) before the cassette-type detector D of 17×17 inches is installed into the holder 6.

In a case where the holder 6 is rotatably attached to the supporting member 7 of the imaging stand 1, the holder 6 comes off on the front side in FIG. 2 if only the circular gear 6g and the linear gear 7a described above are used. Therefore, it goes without saying that a structure or the like is employed to prevent the holder 6 from coming off the supporting member 7 while allowing the above described rotating operation of the holder 6 relative to the supporting member 7.

Further, in a case where a cycloid curve is defined as the "general term for a plane curve obtained as a trajectory of a fixed point on a circle when the circle rotates in accordance with certain rules" while a "cycloid curve" is defined in various ways, the point C moves from C($\alpha$) to C($\beta$) to C($\gamma$) to . . . (or in reverse order) on the trajectory of the fixed point C on the circle (or slightly outside the circle in reality) when the circle rotates in accordance with rules by which the circle (or the circular gear 6g) rotatively moves along a straight line (or the engaging portion 7b of the linear gear 7a), as can be seen from FIGS. 9A and 9B and FIGS. 10A and 10B. Therefore, the point C, which is the center C of a cassette-type detector D of 14×17 inches, moves on a cycloid curve.

Figure 11:
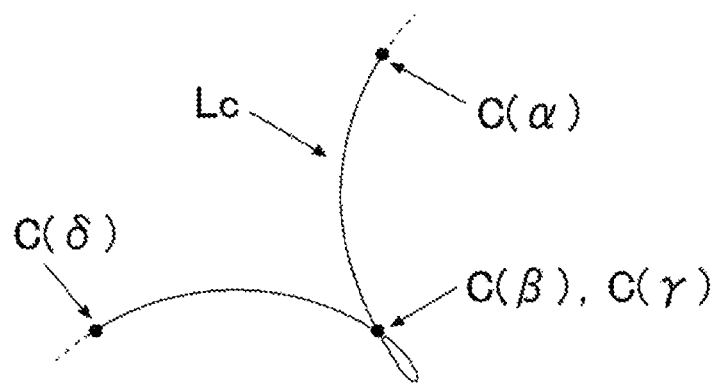
FIG. 11 is a diagram for explaining that the center C of a cassette-type detector of 14×17 inches moves on a cycloid curve when the holder is rotated.

In this embodiment, when the holder 6 is rotated relative to the supporting member 7, the rotation center 6x of the holder 6 linearly moves relative to the supporting member 7 as the holder 6 rotates, as shown in FIGS. 9A and 9B and FIGS. 10A and 10B. In this structure, the center C of the cassette-type detector D of 14×17 inches installed in the holder 6 is moved on the cycloid curve shown in FIG. 11. As the center C of the cassette-type detector D is moved on the cycloid curve, the orientation and the position of the cassette-type detector D can be appropriately changed.

It should be understood that the present invention is not limited to the above described embodiment, and various changes may be made to it without departing from the scope of the invention.

For example, in a case where the imaging stand 1 is a recumbent imaging stand, the imaging stand 1 may be designed so that a cassette-type detector D is not placed in the above described "landscape top" position (see FIG. 16A), which may be applied in a case where the imaging stand 1 is an upright imaging stand. The "top" in the "landscape top" position in the case where the imaging stand 1 is a recumbent imaging stand means the side on which the head of the patient as the subject lying on the top panel of the recumbent imaging stand is located. That is, in recumbent imaging stands and some upright imaging stands, when a cassette-type detector D is placed in a landscape position, the cassette-type detector D is placed in the "portrait" position or the "landscape center" position, but might not be placed in the "landscape top" position where the cassette-type detector D is brought even closer to the head of the patient.

In a case where the present invention is applied to such an imaging stand 1, the rotation angle of the holder 6 is not 0 degrees, but the holder 6 is designed to be rotated 90 to 180 degrees, or is designed to be rotated 90 to 270 degrees if a cassette-type detector D of 17×17 inches is also to be installed.

In a case where a cassette-type detector D of 14×17 inches is installed into the holder 6 in an actual structure of this embodiment, the cassette-type detector D of 14×17 inches is installed into the holder 6 after the holder 6 is rotated 90 degrees in the counterclockwise direction in the situation of the holder 6 shown in FIG. 2 (a situation where any cassette-type detector D is not installed). In this case, the cassette-type detector D of 14×17 inches is placed in the "portrait" orientation and position (see FIG. 17A).

If this situation is regarded as the initial setting, the holder 6 is rotated 90 degrees in the counterclockwise direction relative to the supporting member 7, so that the cassette-type detector D of 14×17 inches is placed in the "landscape center" orientation and position (see FIG. 16B). When the holder 6 is rotated 90 degrees in the opposite direction, which is the clockwise direction, relative to the supporting member 7 in the above described initial setting, the cassette-type detector D of 14×17 inches is placed in the "landscape top" orientation and position (see FIG. 2 and FIG. 16A).

Figure 17B:
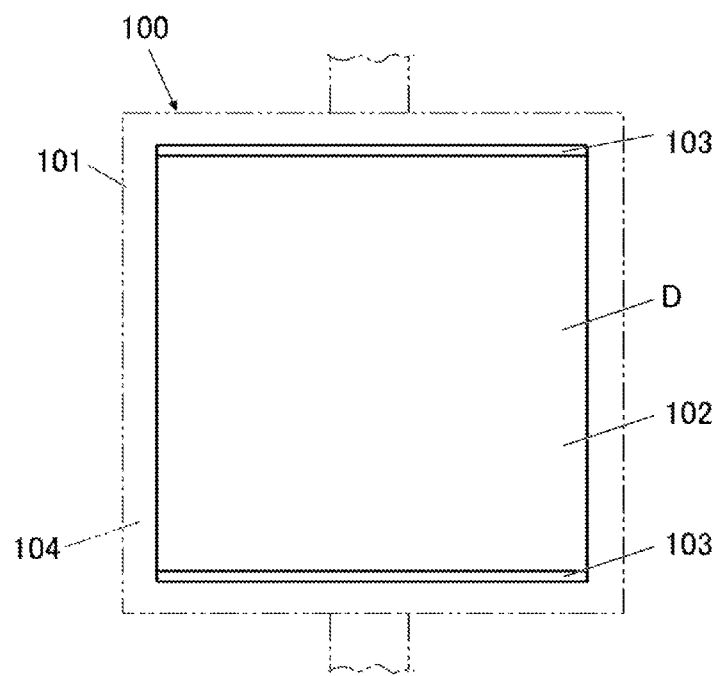
FIG. 17B is a diagram showing a situation where a cassette-type detector of 17×17 inches is installed in a conventional imaging stand.

When the holder 6 is rotated 180 degrees in the counterclockwise direction relative to the supporting member 7 in the above described initial setting, the holder 6 is placed in such a position that a cassette-type detector D of 17×17 inches can be installed. When a cassette-type detector D of 17×17 inches is installed into the holder 6 in that situation, the cassette-type detector D of 17×17 inches is placed in an appropriate position (see FIG. 6 and FIG. 17B).

[Example Structure for Automatically Extending the Distance Between the First Locking Claw and the Second Locking Claws in Accordance with the Rotation Angle of the Holder]

In a case where a cassette-type detector D of 14×17 inches is installed into the holder 6 as shown in FIG. 2, for example, the distance between the first locking claw 6c and the second locking claws 6d is 14 inches. In a case where a cassette-type detector D of 17×17 inches is installed, however, the above distance needs to be extended to 17 inches.

In the structure of the above described embodiment, the rotation angle of the holder 6 in a case where a cassette-type detector D of 14×17 inches is installed is 0 to 180 degrees, and a cassette-type detector D of 17×17 inches is installed in a situation where the holder 6 has been rotated 270 degrees in the counterclockwise direction. Therefore, the distance between the first locking claw 6c and the second locking claws 6d is 14 inches while the rotation angle of the holder 6 is 0 to 180 degrees, but the distance needs to be extended to 17 inches when the rotation angle becomes 270 degrees.

As a result of various studies that were made on a structure for automatically extending the distance between the first locking claw 6c and the second locking claws 6d from 14 inches to 17 inches at the same as the studies on the rotating operation for rotating the holder 6 as described above, the inventor discovered that such a structure can be realized by adding a relatively simple structure to the above described structure of this embodiment. In the description below, an example structure for realizing this is described.

Figure 12:
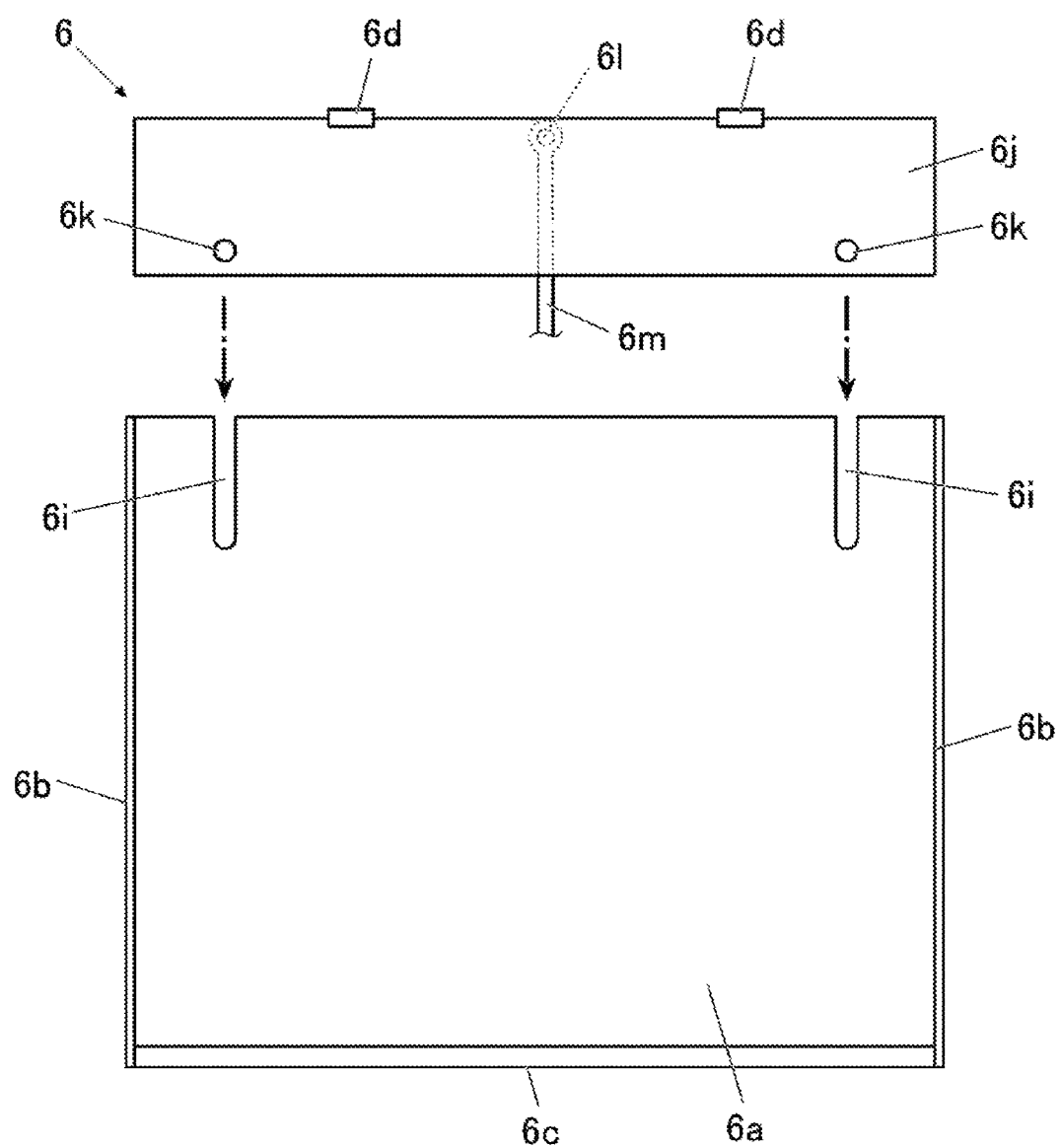

In this case, the holder 6 is first designed as shown in FIG. 12, for example. Specifically, the holder 6 is designed to include the back surface plate 6a, the restricting plates 6b, the first locking claw 6c, and the like, as in the above described embodiment. Although not shown in the drawing, the springs 6e are also attached to the first locking claw 6c, as in the holder 6 shown in FIG. 2. At portions on the opposite side (the upper side in FIG. 12) of the back surface plate 6a from the first locking claw 6c, slits 6i are formed to extend parallel to the restricting plates 6b, for example.

As shown in FIG. 12, a slide plate 6j is provided separately from the back surface plate 6a. Convex portions 6k are formed in positions on the slide plate 6j, the positions corresponding to the slits 6i of the back surface plate 6a. The convex portions 6k of the slide plate 6j are then inserted into the slits 6i of the back surface plate 6a so that the convex portions 6k can move inside the slits 6i in the extending direction of the slits 6i (or the vertical direction in FIG. 12). In this manner, the slide plate 6j is movably attached to the back surface plate 6a.

In the example shown in FIG. 12, the slide plate 6j is attached to the back surface side of the back surface plate 6a or the back side in FIG. 12, so that the convex portions 6k protrude forward in the drawing. In this case, the second locking claws 6d are attached to the slide plate 6j. Springs or the like (not shown) are also attached to the second locking claws 6d. The second locking claws 6d are attached to the slide plate 6j so as to be movable in the vertical direction in FIG. 12, and are pushed toward the first locking claw 6c (or downward in FIG. 12) by the springs or the like, as in the above described embodiment (see FIG. 2).

A shaft portion 6l is provided in the center portion on the back surface side of the slide plate 6j in the horizontal direction in FIG. 12, and one end of a stick-like member 6m is rotatably attached to the shaft portion 6l. As will be described later, the stick-like member 6m pushes and pulls the shaft portion 6l, so that the slide plate 6j moves in the extending direction of the slits 6i (or the vertical direction in FIG. 12) relative to the back surface plate 6a. It should be noted that the stick-like member 6m neither expands nor contracts.

Figure 13:
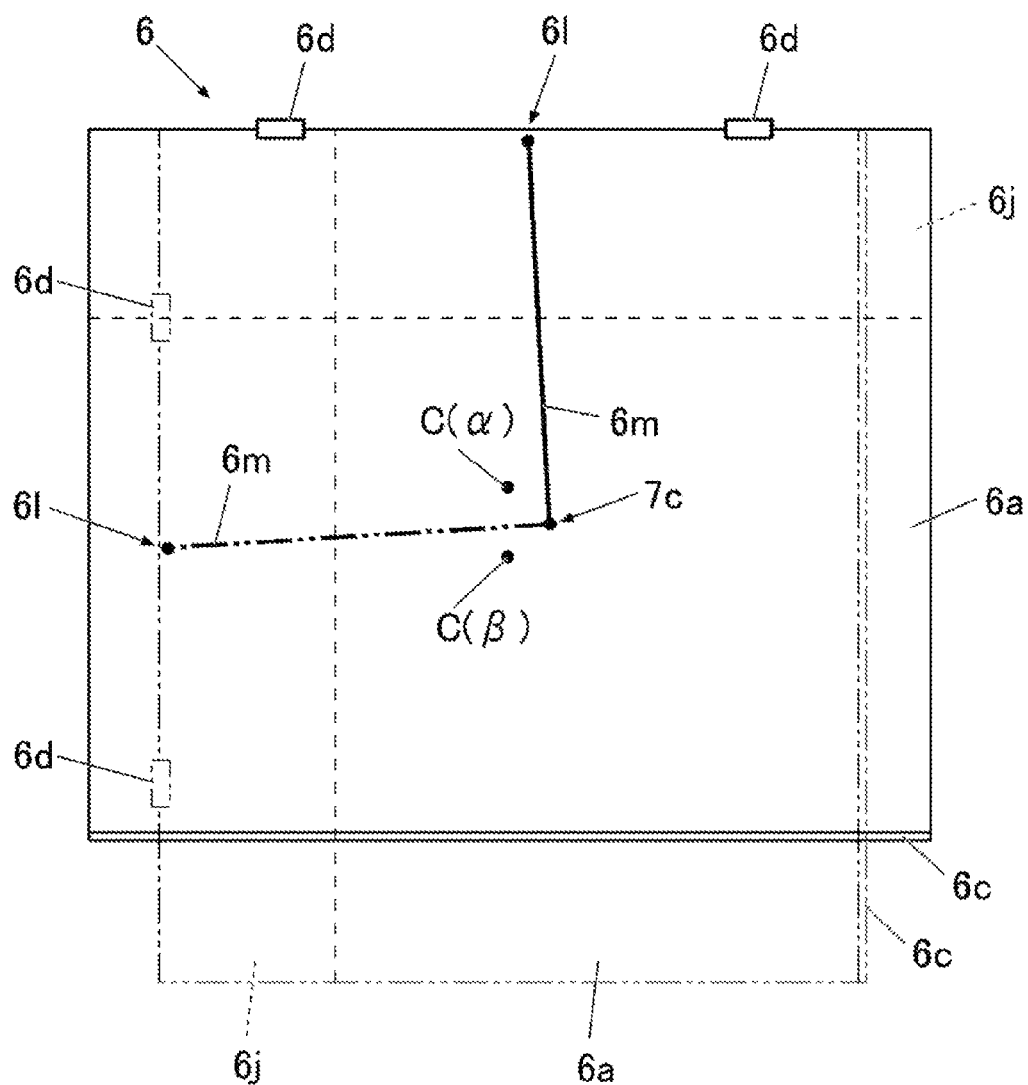
FIG. 13 is a diagram showing positional relationships among the stick-like member, a first locking claw, second locking claws, and others in cases where the rotation angle of the holder is 0 degrees and 90 degrees.

As shown in FIG. 13 (see the portion represented by the solid line in FIG. 13), the other end of the stick-like member 6m is rotatably attached to a shaft portion 7c of the supporting member 7 (not shown in FIG. 13, but shown in FIG. 14, which will be described later). The shaft portion 7c is provided in a position near the above described point C(α) and the point C(β). More accurately, the shaft portion 7c is provided in a location on the supporting member 7, the location being at a distance of 0.75 inches to the right of the middle position between the point C(α) and the point C(β) in the vertical direction, the point C(α) and the point C(β) being at a distance of 1.5 inches from each other in the vertical direction in FIG. 13. As for the positional relationship with the above described rotation center 6x of the holder 6, the shaft portion 7c is located in a position immediately below the rotation center 6x (equal to the center of the circular gear 6g) of the holder 6 shown in FIG. 9A in the supporting member 7, and is located in a position on a side (to the right) of the rotation center 6x of the holder 6 in a case where the holder 6 has been rotated 90 degrees in the counterclockwise direction as shown in FIG. 9B.

In a case where the holder 6 is placed in a position where the rotation angle is 0 degrees, the stick-like member 6m has such a length relative to the back surface plate 6a that the slide plate 6j movable relative to the back surface plate 6a is located in a position where the distance between the first locking claw 6c and the second locking claws 6d becomes 14 inches.

So as to prevent interference between the above described rotating operation of the circular gear 6g relative to the linear gear 7a and the rotating operation of the stick-like member 6m with rotation of the holder 6 in this case, the circular gear 6g and the linear gear 7a can be provided on the back surface side of the supporting member 7, and the stick-like member 6m and the shaft portion 7c can be provided on the surface side (the side on which the holder 6 is provided) of the supporting member 7, as shown in FIG. 14, for example. FIG. 14 is a side view of the holder 6 at the rotation angle of 0 degrees and others, seen from the left side in FIG. 13.

When the holder 6 is rotated 90 degrees in the counterclockwise direction as described above in the situation shown in FIG. 13 or the situation where the rotation angle of the holder 6 is 0 degrees, the stick-like member 6m rotates about the shaft portion 7c on the supporting member 7. As shown in FIG. 13 (see the portion indicated by the double-dot-and-dash lines in FIG. 13), with the positional relationship between the back surface plate 6a and the slide plate 6j of the holder 6 being considered invariable, the distance between the shaft portion 6l on the slide plate 6j and the shaft portion 7c on the supporting member 7 in a situation where the holder 6 has been rotated 90 degrees in the counterclockwise direction to be located in the "portrait" position is calculated, and the calculated distance is exactly equal to the length of the stick-like member 6m. That is, even when the holder 6 is rotated 90 degrees in the counterclockwise direction, the shaft portion 6l of the slide plate 6j is not pushed by the stick-like member 6m, and the positional relationship between the slide plate 6j and the back surface plate 6a does not change. Therefore, the holder 6 is rotated 90 degrees in the counterclockwise direction, while the distance between the first locking claw 6c and the second locking claws 6d is maintained at 14 inches.

Figure 15:
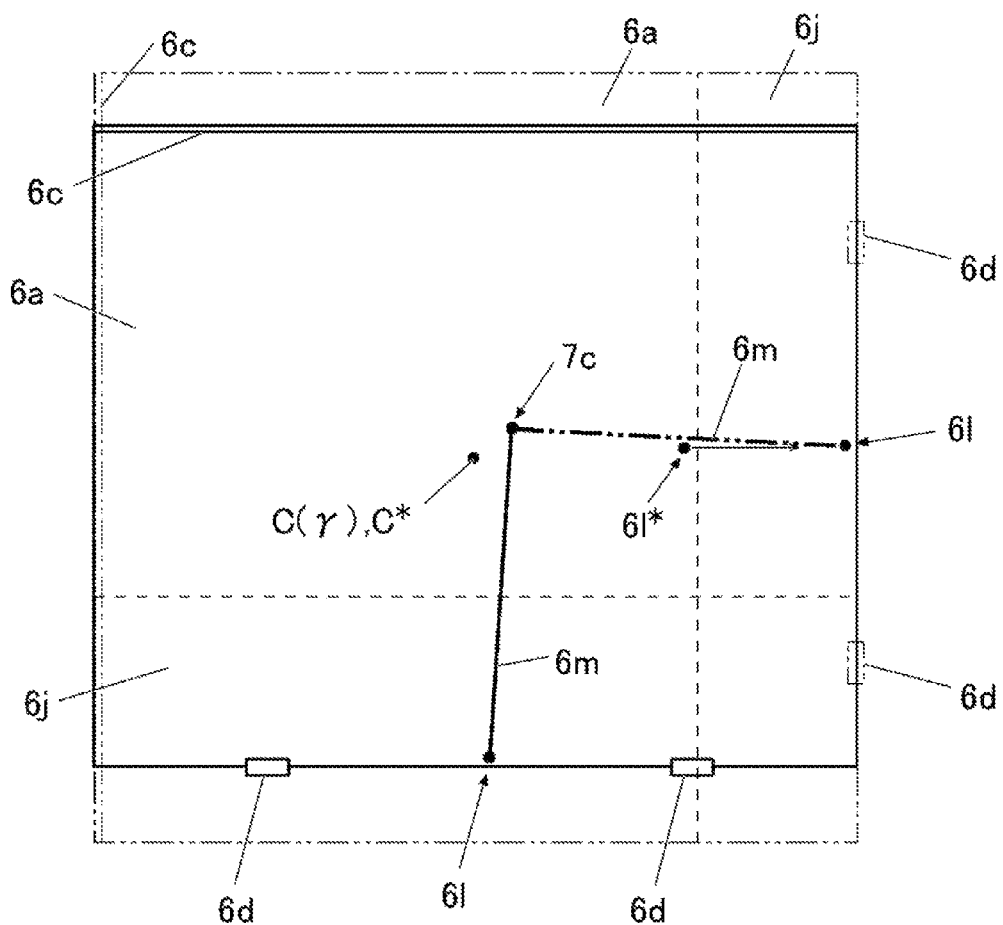
FIG. 15 is a diagram showing positional relationships among the stick-like member, the first locking claw, the second locking claws, and others in cases where the rotation angle of the holder is 180 degrees and 270 degrees.

When the holder 6 is further rotated 90 degrees (180 degrees in total) in the counterclockwise direction in the above situation where the rotation angle of the holder 6 is 90 degrees, the stick-like member 6m rotates about the shaft portion 7c on the supporting member 7 as shown in FIG. 15 (see the portion indicated by the solid line in FIG. 15). With the positional relationship between the back surface plate 6a and the slide plate 6j of the holder 6 being also considered invariable in this case, the distance between the shaft portion 6l on the slide plate 6j and the shaft portion 7c on the supporting member 7 in a situation where the holder 6 has been rotated 90 degrees in the counterclockwise direction to be located in the "landscape center" position is calculated, and the calculated distance is exactly equal to the length of the stick-like member 6m. That is, even when the holder 6 is further rotated 90 degrees in the counterclockwise direction in this case, the shaft portion 6l of the slide plate 6j is not pushed by the stick-like member 6m, either, and the positional relationship between the slide plate 6j and the back surface plate 6a does not change, either. Therefore, the holder 6 is rotated 90 degrees in the counterclockwise direction, while the distance between the first locking claw 6c and the second locking claws 6d is maintained at 14 inches.

In a case where a cassette-type detector D of 14×17 inches is installed into the holder 6 in the above described structure, as long as the rotation angle of the holder 6 is in the range of 0 to 180 degrees, the positional relationship between the back surface plate 6a of the holder 6 and the slide plate 6j supported by the stick-like member 6m does not change, and the distance between the first locking claw 6c and the second locking claws 6d is maintained precisely at 14 inches. Therefore, in a situation where the holder 6 is rotated within the rotation angle range (0 to 180 degrees), the cassette-type detector D of 14×17 inches is firmly interposed between the first locking claw 6c and the second locking claws 6d of the holder 6, and is held in the holder 6. Accordingly, it is possible to firmly maintain the state where the cassette-type detector D of 14×17 inches is held in the holder 6.

In a case where the holder 6 is further rotated 90 degrees (270 degrees in total) (see the portion indicated by the double-dot-and-dash lines in FIG. 15) in the above situation or a situation where the holder 6 has been rotated 180 degrees in the counterclockwise direction, if the positional relationship between the back surface plate 6a and the slide plate 6j of the holder 6 does not change as in the above cases, the shaft portion 6l on the slide plate 6j comes to the position denoted by 6l* in FIG. 15, but the distance between the point 6l* and the shaft portion 7c on the supporting member 7 is apparently shorter than the length of the stick-like member 6m. Therefore, in this case, the shaft portion 6l of the slide plate 6j is pushed to the right in the drawing by the stick-like member 6m, and the slide plate 6j moves (slides) to the right in the drawing relative to the back surface plate 6a.

When the movement distance of the slide plate 6j relative to the back surface plate 6a is calculated from the length of the stick-like member 6m and the like, the calculated distance is 3 inches, and the distance between the first locking claw 6c and the second locking claws 6d, which was 14 inches in the above case, is extended to 17 inches automatically (or simply by rotating the holder 6). Accordingly, a cassette-type detector D of 17×17 inches can be precisely installed into the holder 6 in this situation or the situation where the holder 6 has been rotated 270 degrees in total in the counterclockwise direction, and the holder 6 can firmly maintain the cassette-type detector D of 17×17 inches in this state.

It should be noted that the holder 6 is not limited to the structure including the back surface plate 6a, the slide plate 6j, and the like shown in FIG. 12, but may have any kind of structure, as long as the distance between the first locking claw 6c and the second locking claws 6d can be extended with the stick-like member 6m in accordance with the rotating operation of the holder 6 as described above.

[Automatic Setting and the Like of a Field of Radiation to be Emitted to a Cassette-Type Detector]

In a case where imaging is performed by emitting radiation from an irradiation apparatus to a cassette-type detector D installed in the above described imaging stand 1 via a subject, the radiation field is normally narrowed by a collimator so that healthy body parts other than the affected area or the involved area of the patient as the subject are not exposed to radiation, and the dose of radiation to which the patient is exposed does not exceed the necessary amount.

Conventionally, the region exposed to radiation from an irradiation apparatus is also irradiated with visible light from a halogen lamp or the like. While looking at the irradiation, a radiological technologist or the like adjusts the position and the irradiation direction of the radiation emitted toward the subject by manually adjusting the position and the orientation of the irradiation apparatus, or narrows the radiation field by operating the collimator or the like, so that the radiation is emitted to an appropriate region including the affected area or the like of the patient. However, if this operation is automatically performed by the irradiation apparatus, the user-friendliness of the irradiation apparatus can increase.

In view of this, U.S. Pat. No. 7,806,591, for example, discloses a technology for automatically detecting the SID (Source Image receptor Distance) or the distance between the focal point of the radiation source (source) of the irradiation apparatus and the image receiving surface of a cassette-type detector D (image receptor) by providing a reflective member in the cassette-type detector D and sensing the distance to the reflective member. The image receiving surface of the cassette-type detector D may be the above described radiation incidence surface R (see FIG. 2 and others) of the cassette-type detector D, but more accurately, is the surface on which radiation detecting elements are two-dimensionally arranged on a sensor substrate in the cassette-type detector D.

However, where the cassette-type detector D is installed in the imaging stand 1, the reflective member provided in the cassette-type detector D cannot be detected from the irradiation apparatus by the above method.

U.S. Pat. No. 7,545,914 discloses a technology for sensing the position of each apparatus and the position of a patient by providing a camera or the like in the imaging room where the irradiation apparatus, the imaging stand 1, and the like are set, and imaging the inside of the imaging room, for example. In this case, however, if there is a person such as a radiological technologist or an attendant in addition to the patient, or if there is an obstacle, the position of each apparatus and the position of the patient might not be detected. Also, complicated image processing becomes necessary, and it is difficult to estimate the optical axis of radiation emitted from the irradiation apparatus. As a result, the position of the irradiation apparatus to be used is limited.

In view of this, the inventor has suggested a technology for detecting the rotating direction of the collimator and the optical axis direction or the like of emitted radiation by adding a camera to the collimator of the irradiation apparatus, and analyzing images captured by the camera (see JP 2011-92612 A and others). As a result of further studies on such technologies, the inventor succeeded in developing a technology for automatically and appropriately setting a radiation field with a collimator by detecting the position of the radiation source of the irradiation apparatus, the rotating direction of the collimator, the optical axis direction of emitted radiation, and the like. In the description below, this technology is described.

Figure 18:
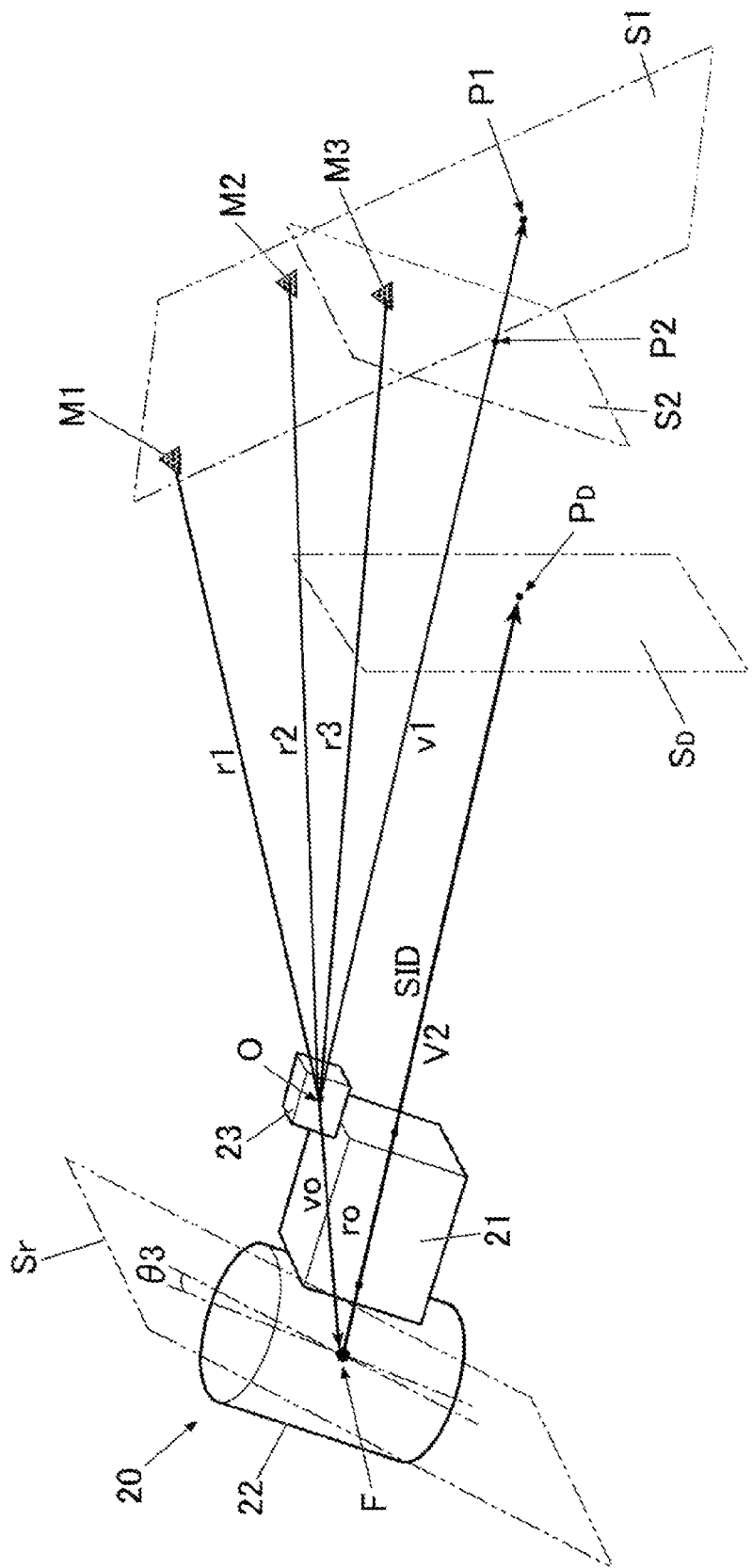
FIG. 18 is a diagram for explaining a method of calculating the distance SID between the focal point of the radiation source of an irradiation apparatus and the image receiving surface of a cassette-type detector by using a depth camera.

As shown in FIG. 18, in an irradiation apparatus 20, a collimator 21 that has a diaphragm or the like provided therein and narrows the field of radiation to be emitted from the irradiation apparatus 20 is attached to a cylindrical unit 22 in which the radiation source (not shown, but see the radiation source 40 shown in FIGS. 23A and 23B, which will be described later, for example) of the irradiation apparatus 20 is housed. Although not shown in the drawing, the collimator 21 is designed to be able to automatically and accurately change the degree of opening of the aperture of the diaphragm (the subject or the like is exposed only to radiation that has passed through this aperture from the irradiation apparatus 20) by a known technique.

An imaging measurement unit 23 such as a depth camera that can capture an image and measure the distance to the imaged subject is attached to the collimator 21. Although the imaging measurement unit 23 is described below as the depth camera 23, the imaging measurement unit 23 is not necessarily formed with a depth camera, and is not particularly limited to a specific structure, as long as the imaging measurement unit 23 can capture an image and measure the distance to the imaged subject.

The collimator 21 and the depth camera 23 are secured to the cylindrical unit 22 and the collimator 21 of the irradiation apparatus 20, respectively. The positional relationship between the focal point F of the radiation source of the irradiation apparatus 20 and the imaging center O of the depth camera 23 is invariable, and the distance r0 between the focal point F and the imaging center O, and the offset vector v0 from the imaging center O to the focal point F of the radiation source of the irradiation apparatus 20 are known in advance.

Markers M1, M2, and M3 are formed in positions that do not have any patient or any other apparatus interposed between the irradiation apparatus 20 and the positions, and are not affected by the use of an apparatus or the like. Examples of such positions include upper portions of a wall surface of the imaging room where the irradiation apparatus 20 is set, or upper end portions of the stand 3 (see FIGS. 1A and 1B) of the imaging stand 1. The coordinates (or the latitudes, the longitudes, and the heights from the floor surface (or the altitudes)) of the respective centers of the markers M1 to M3 in the real space are measured beforehand and are known. Shapes, colors, and the like of the markers M1 to M3 are determined as appropriate.

In the above described structure, the irradiation apparatus 20 automatically detects the position of the focal point F of the radiation source, the irradiation direction of radiation, the distance to the cassette-type detector D installed in the imaging stand 1 (or the above described SID; hereinafter, this distance will be referred to as the distance SID), and the like, and automatically and accurately set a field of radiation. Referring now to FIG. 18, this technique is described below. The description below is based on the assumption that the irradiation apparatus 20 performs all processes including the process of calculating the distance SID. However, a structure (or a radiological imaging system including the irradiation apparatus 20 and a processing apparatus) may be formed so as to transmit data and the like from the irradiation apparatus 20 or the like to an external processing apparatus (not shown), and perform the process of calculating the distance SID with the processing apparatus.

First, the markers M1 to M3 are imaged by the depth camera 23. In a case where the markers M1 to M3 are colored, the depth camera 23 captures a color image of the markers M1 to M3, and detects the positions of the markers M1 to M3 in the image. The distances r1 to r3 to the respective centers of the markers M1 to M3 are measured and acquired with the depth camera 23. As the coordinates of the respective centers of the markers M1 to M3 in the real space are known as described above, the coordinates of the imaging center O of the depth camera 23 are determined from the distances r1 to r3 and the coordinates of the respective centers of the markers M1 to M3 in the real space.

To calculate the above described distance SID, a process of determining the coordinates of the focal point F of the radiation source of the irradiation apparatus 20 in the real space is performed. In this case, the coordinates of the focal point F of the radiation source of the irradiation apparatus 20 in the real space cannot be determined, unless not only the coordinates of the imaging center O of the depth camera 23 determined in the above described manner and the above described offset vector v0, but also the orientation of the depth camera 23 (or a vertical angle $\theta 1$ and a horizontal angle $\theta 2$ of the camera direction v1 described later), and the rotation angle (or the overall rotation angle $\theta 3$ described later) of the entire irradiation apparatus 20 about the irradiation direction of radiation (or the X-ray direction v2 described later) are known.

In view of this, the orientation of the depth camera 23 is first determined. As the one plane that passes through three point can be determined, the virtual plane S1 that passes through the markers M1 to M3 are set in the real space. Meanwhile, the pixel positions of the markers M1 to M3 in the image captured by the depth camera 23 are determined, and the positional relationship among the respective pixel positions, and the positional relationship between each pixel position and the image center are determined. The positional relationships in the image are then applied to the virtual plane S1 that is set in the real space as described above, and the coordinates of a point P1 in the real space are determined. The point P1 is formed by projecting the image center onto the virtual plane S1.

The direction from the imaging center O of the depth camera 23 toward the point P1 (or the direction of the vector v1 from the imaging center O toward the point P1) will be hereinafter referred to as the camera direction v1. The depth camera 23 is attached to the collimator 21 in advance, so that the camera direction v1 becomes parallel to the irradiation direction v2 (hereinafter referred to as the X-ray direction v2) of radiation from the irradiation apparatus 20.

Figure 19:
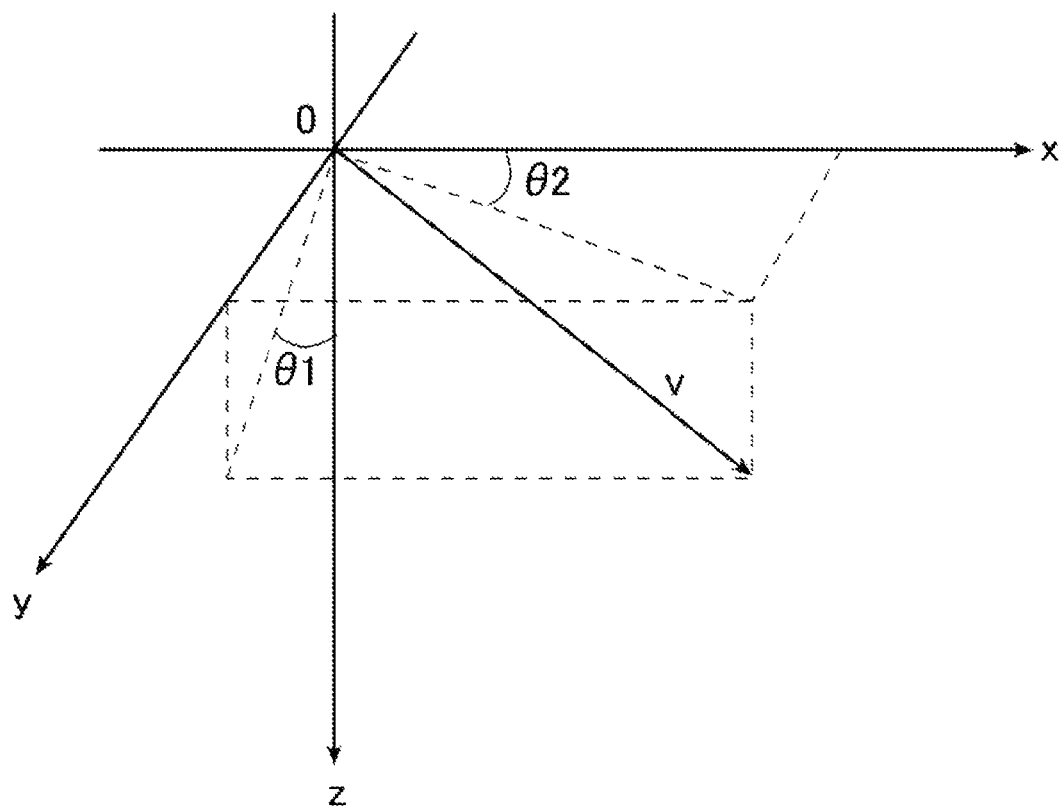
FIG. 19 is a diagram for explaining a vertical angle θ1 and a horizontal angle θ2 of a vector.

As shown in FIG. 19, the angles $\theta 1$ and $\theta 2$ of the respective vectors formed by projecting a vector v onto the reference vertical plane (the y-z plane in FIG. 19) and the reference horizontal plane (the x-y plane in FIG. 19) with respect to the vertical axis (the z-axis in FIG. 19) and the reference horizontal axis (the x-axis in FIG. 19) are referred to as the vertical angle $\theta 1$ and the horizontal angle $\theta 2$ of the vector v, respectively. Also, as shown in FIG. 18, the angle $\theta 3$ of the entire irradiation apparatus 20 rotated about the reference axis in an overall rotation plane Sr is referred to as the overall rotation angle $\theta 3$.

After the coordinates of the point P1 in the real space are determined as described above, the vector v1 (see FIG. 18) connecting the imaging center O and the point P1 or the camera direction v1 is determined, as the coordinates of the imaging center O of the depth camera 23 in the real space are already known. Accordingly, the vertical angle $\theta 1$ and the horizontal angle $\theta 2$ of the camera direction v1 can be determined as shown in FIG. 19.

With the camera direction v1 being the normal line, a virtual plane S2 that passes through one marker M (the marker M3 in the case shown in FIG. 18) among the three markers M1 to M3 is set in the real space. The coordinates of the point P2 formed by projecting the image center onto the plane S2 are then determined in the real space. The overall rotation angle $\theta 3$ is then calculated from the coordinates of the point P2 in the real space and the coordinates of the marker M3 in the real space. In this manner, it is possible to recognize that the entire irradiation apparatus 20 has been rotated by the overall rotation angle θ3 about the reference axis in the overall rotation plane Sr.

The above described offset vector v0 (see FIG. 18) is defined as the vector (va, vb, vc) from the imaging center θ of the depth camera 23 toward the focal point F of the radiation source of the irradiation apparatus 20 in a case where the vertical angle θ1 and the horizontal angle θ2 of the camera direction v1, and the overall rotation angle θ3 of the entire irradiation apparatus 20 are all 0 degrees. Therefore, the actual orientation of the offset vector v0 is calculated based on the actual vertical angle θ1, horizontal angle θ2, and overall rotation angle θ3, which have been determined in the above described manner. That is, the respective components va*, vb*, and vc* of the actual offset vector v0 are determined from the respective components va, vb, and vc of the offset vector v0=(va, vb, vc), and the above described vertical angle θ1, horizontal angle θ2, and overall rotation angle θ3.

The coordinates of the focal point F of the radiation source of the irradiation apparatus 20 can be calculated based on the determined actual offset vector v0 and the already determined coordinates of the imaging center O of the depth camera 23 in the real space. In the above manner, the coordinates of the focal point F of the radiation source of the irradiation apparatus 20 in the real space are first calculated.

In a case where the offset vector v0 is defined as a unit vector (the length being 1) of the vector from the imaging center O of the depth camera 23 toward the focal point F of the radiation source of the irradiation apparatus 20, the vector calculated by multiplying the offset vector v0 by the distance r0 between the imaging center O of the depth camera 23 and the focal point F of the radiation source of the irradiation apparatus 20 is of course used in the above described calculation.

Meanwhile, in the imaging stand 1 (see FIGS. 1A and 1B, and others), the cassette-type detector D installed in the bucky 2 can move up and down along the stand 3 of the imaging stand 1, as described above. In that case, the cassette-type detector D moves up and down in a virtual plane $S_D$ (see FIG. 18) in the real space. Hereinafter, the virtual plane $S_D$ will be referred to as the operation plane $S_D$ of the cassette-type detector D. The above described distance SID is the distance from the focal point F of the radiation source of the irradiation apparatus 20 having its coordinates in the real space determined in the above described manner, to the operation plane $S_D$ of the cassette-type detector D.

The X-ray direction v2 or the irradiation direction v2 of radiation from the focal point F of the radiation source of the irradiation apparatus 20 is parallel to the camera direction v1 as described above, and the camera direction v1 has already been calculated as the vector that connects the imaging center O of the depth camera 23 and the point P1 in the virtual plane S1 as described above. Therefore, the vector of the X-ray direction v2 (the components of the vector are the same as the respective components of the camera direction v1) is extended from the focal point F of the radiation source of the irradiation apparatus 20 having its coordinates in the real space determined in the above described manner, and the intersection $P_D$ with the operation plane $S_D$ of the cassette-type detector D is determined. The distance between the focal point F of the radiation source of the irradiation apparatus 20 and the point $P_D$ in the operation plane $S_D$ of the cassette-type detector D determined in the above described manner is the distance SID to be determined.

In the above described manner, the distance SID from the focal point F of the radiation source of the irradiation apparatus 20 to the image receiving surface of the cassette-type detector D can be automatically and accurately calculated by the irradiation apparatus 20 or an external processing apparatus that has obtained data from the irradiation apparatus 20.

Once the above distance SID is calculated, radiation is accurately emitted from the irradiation apparatus 20 to the cassette-type detector D in the above described operation plane $S_D$. Also, it is possible to determine to what extent radiation should be emitted from the irradiation apparatus 20 in the horizontal direction and the vertical direction so as to prevent radiation exposure outside the cassette-type detector D. That is, the field of radiation to be emitted can be determined. In this case, the information about the size, the orientation, and the position (such as the above described "landscape top", "portrait", or "landscape center" position) of the cassette-type detector D installed in the imaging stand 1 is necessary. Therefore, this information is input to the irradiation apparatus 20 by a radiological technologist or from an external device such as a console.

In this manner, the irradiation apparatus 20 calculates the field of radiation to be emitted in the horizontal direction and the vertical direction based on the information, so that the degree of opening of the aperture of the diaphragm in the collimator 21 can be adjusted to automatically and accurately set the radiation field.

Thereafter, the information about the height (or the altitude as in the description below) of the cassette-type detector D in the imaging stand 1 from the floor surface is input to the irradiation apparatus 20 by a radiological technologist or the like, the height of the bucky 2 of the imaging stand 1 from the floor surface is determined from an image analysis conducted on an image captured by the depth camera 23 or the like, or the height of the cassette-type detector D from the floor surface is determined by providing a marker on the bucky 2 separately from the above described markers M1 to M3 and determining the height of the bucky 2 of the imaging stand 1 from an image of the marker imaged by the depth camera 23 in the same manner as above.

The irradiation apparatus 20 changes the X-ray direction v2 as the irradiation direction of radiation by changing the above described vertical angle θ1 and horizontal angle θ2, or adjusts the overall rotation angle θ3 by rotating the cylindrical unit 22 and the irradiation apparatus 20, where necessary. In this manner, the radiation emitted from the focal point F of the radiation source precisely reaches the cassette-type detector D existing at the above determined height from the floor surface.

As the irradiation apparatus 20 or the radiological imaging system including the irradiation apparatus 20 and a processing apparatus has the above described structure, the irradiation apparatus 20 or the processing apparatus that has obtained data from the irradiation apparatus 20 automatically and accurately calculates the distance SID from the focal point F of the radiation source of the irradiation apparatus 20 to the image receiving surface of the cassette-type detector D. Based on the distance SID, the irradiation apparatus 20 emits radiation to the cassette-type detector D, and automatically and appropriately sets a radiation field so that radiation is not emitted to any region outside the cassette-type detector D. Accordingly, the irradiation apparatus 20 can have higher user-friendliness.

So as to set a radiation field with even higher precision, and expose only the necessary area including the affected area or the involved area of the patient as the subject to radiation while preventing the healthy body parts from being exposed to radiation, a structure for setting a narrower radiation field with high precision by inputting necessary information to the irradiation apparatus 20, for example, may be added to the above described technology.

In this case, the patient as the subject is invariably positioned between the focal point F of the radiation source of the irradiation apparatus 20 and the cassette-type detector D at a time of imaging. Accordingly, in a case where an object is detected at a location closer to the irradiation apparatus 20 than to the cassette-type detector D (or at a shorter distance than the distance SID) as a result of distance measurement with the depth camera 23 at the time of imaging, the object can be recognized as the subject (or the patient). At this point, the patient as the subject invariably exists near the imaging stand 1. Since the operation plane $S_D$ (see FIG. 18) of the cassette-type detector D is already known as described above, the space in which the subject exists can be assumed to be near the operation plane $S_D$ of the cassette-type detector D or near the imaging stand 1 as detected from the operation plane $S_D$ and is on the side of the irradiation apparatus 20. The space can be readily determined, because whether the space is located near the cassette-type detector D or the imaging stand 1 on the side of the irradiation apparatus 20 can be determined by the depth camera 23. At a time of imaging, radiation is invariably emitted toward the subject. Accordingly, by using the above information, the irradiation apparatus 20 can automatically and appropriately set the radiation field so that radiation will be emitted only to the smallest possible area to image the subject.

If the irradiation apparatus 20 obtains information indicating the exact location of the affected area or the involved area in the body of the patient, the irradiation apparatus 20 can further narrow the radiation field so that radiation will be emitted only to the necessary area including the affected area or the like.

Alternatively, the irradiation apparatus 20 can also be designed to set the radiation field so that radiation will be emitted only to the cassette-type detector D as described above, and then perform an operation to narrow the radiation field so that a radiological technologist or the like can manually apply radiation only to the necessary area including the affected area or the involved area of the patient as the subject.

In the above described example, a cassette-type detector D is installed in the so-called upright imaging stand 1 shown in FIGS. 1A and 1B and others, and the cassette-type detector D moves up and down with vertical movement of the bucky 2, with the image receiving surface of the cassette-type detector D facing substantially in the horizontal direction. However, there are cases where a cassette-type detector D moves up and down, with the image receiving surface of the cassette-type detector D facing upward, as in a case where a cassette-type detector D is installed in a so-called recumbent imaging stand.

In such a case, a marker that is separate from the above described markers M1 to M3 is provided on a portion that moves up and down with the cassette-type detector D and can be imaged by the depth camera 23 of the irradiation apparatus 20, such as the bucky having the cassette-type detector D installed therein or the top panel of the recumbent imaging stand (or the panel on which the subject is to lie down). The height of the bucky or the top panel of the recumbent imaging stand from the floor surface is then determined from an image of the marker imaged by the depth camera 23 in the same manner as above. After that, the height of the cassette-type detector D from the floor surface can be determined, or the above described distance SID can be calculated.

[Technique for Accurately Calculating the Dose of Radiation to which a Subject has been Exposed]

Concerning the above described irradiation apparatus 20, there are many cases where a DAP (Dose Area Product) meter for measuring a dose area product of radiation emitted from the irradiation apparatus 20 is attached to the irradiation apparatus 20. However, while the dose area product of radiation emitted from the irradiation apparatus 20 is measured with this DAP meter, the dose area product of radiation emitted to the patient as the subject or the dose of radiation to which the subject has been exposed cannot be accurately determined with the DAP meter.

Figure 20:
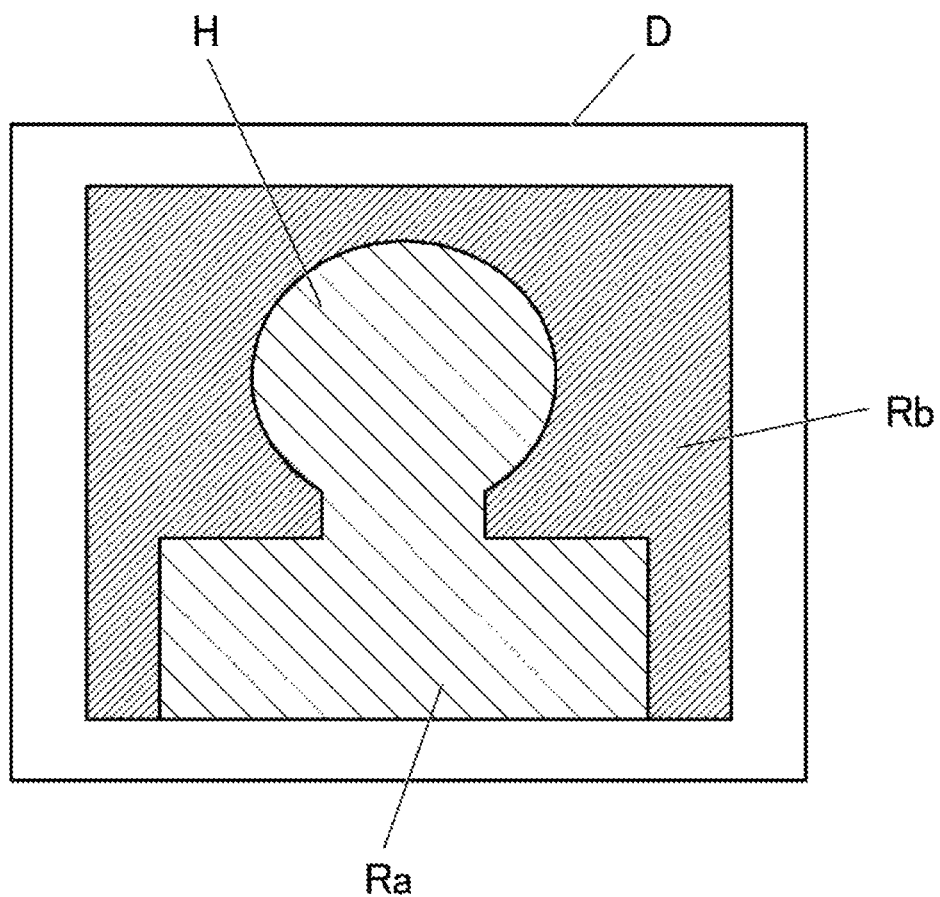
FIG. 20 is a diagram showing a region Ra of an imaged subject and a region Rb outside the imaged subject in a case where radiation is emitted and enters a cassette-type detector.

In this case, for example, the field of radiation emitted from the irradiation apparatus 20 is narrowed. As shown in FIG. 20, if radiation is emitted so that all the emitted radiation enters the cassette-type detector D via a subject H (or if radiation is emitted so that the emitted radiation does not leak out of the cassette-type detector D), a captured image is analyzed to calculate the area of the region Ra of the imaged subject H and the area of the region Rb outside the imaged subject H, and the actual dose of radiation to which the patient as the subject H has been exposed can be calculated by multiplying the dose area product measured with the DAP meter by Ra/(Ra+Rb).

In actual imaging, however, radiation is not necessarily emitted so that the field of radiation emitted from the irradiation apparatus 20 falls within the cassette-type detector D as described above. Therefore, in any type of imaging, there is a demand for development of a technique for accurately calculating an actual dose of radiation to which a subject H has been exposed. In view of such circumstances, the inventor made studies on techniques and the like for accurately calculating the dose of radiation to which a subject H has been exposed. As a result, the inventor has discovered that such a technique can be realized with the structure described below.

Figure 21:
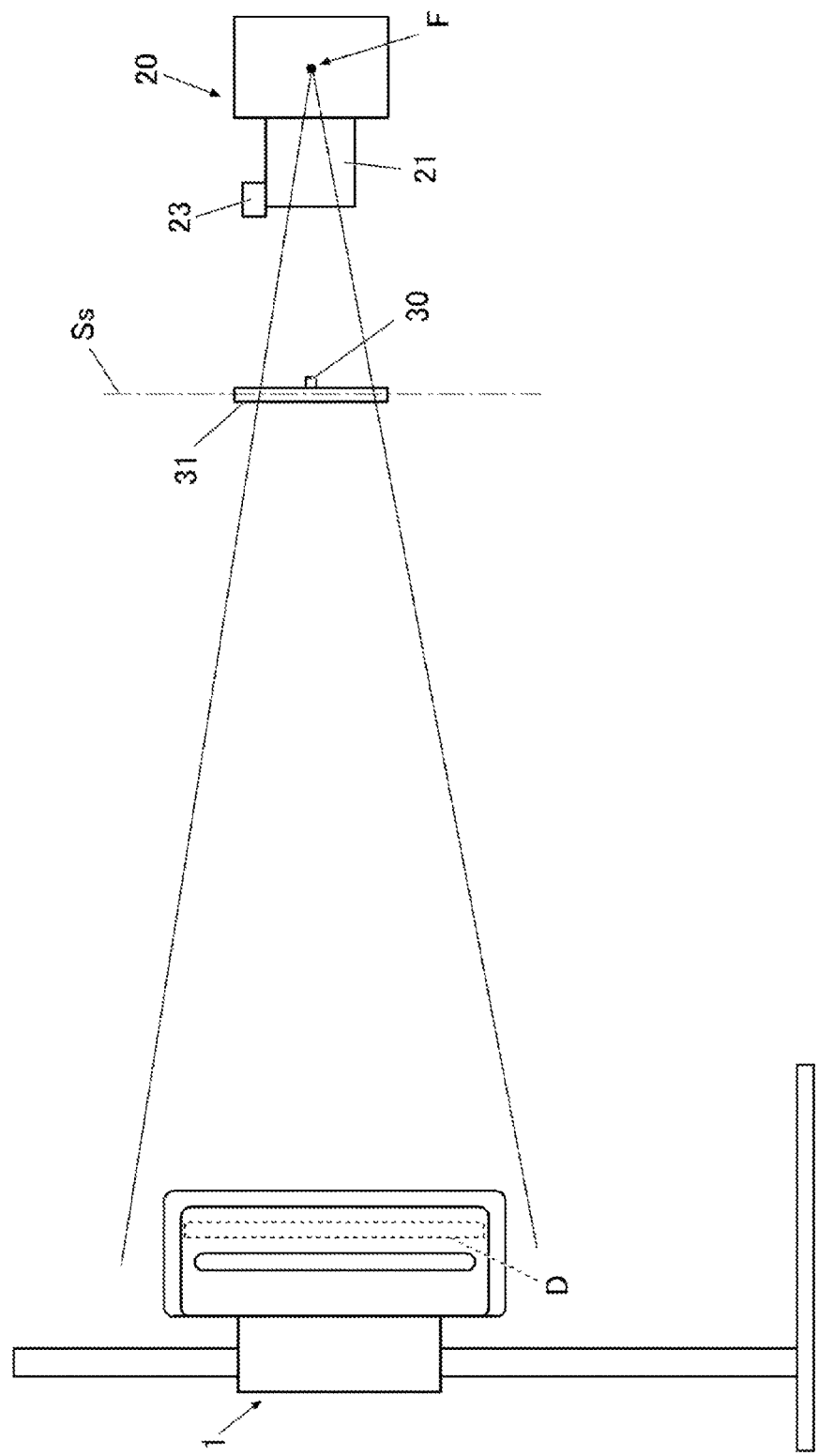
FIG. 21 is a diagram showing an example structure designed to measure the irradiation range of radiation with a radiation sensor.

In a case where imaging is performed with a cassette-type detector D installed in the above described imaging stand 1, for example, a radiation sensor 30 that detects radiation emitted from the irradiation apparatus 20 is provided between the irradiation apparatus 20 and the imaging stand 1, as shown in FIG. 21. At this point, the radiation sensor 30 is attached to a supporting plate 31, for example, and is designed to move two-dimensionally on a predetermined virtual plane $S_S$ in the real space when the supporting plate 31 is moved by a moving device (not shown).

It should be noted that the distance rs between the radiation sensor 30 and the focal point F of the radiation source of the irradiation apparatus 20 is known in advance. Alternatively, the radiation sensor 30 can be designed to be movable only in the vertical direction (or one-dimensionally), for example, and estimate the horizontal range of radiation emitted from the irradiation apparatus 20 in accordance with the vertical range of radiation to be emitted from the irradiation apparatus 20 and the horizontal-to-vertical ratio of the radiation field set by the collimator 21 of the irradiation apparatus 20, the vertical range of the radiation emitted from the irradiation apparatus 20 being detected by the radiation sensor 30 as described below. In this case, the supporting plate 31 to which the radiation sensor 30 is attached can be the covering plate of a covering plate unit for long-time imaging disclosed in JP 2013-154146 A (see the covering plate 61 of the covering plate unit 60 in the publication), for example. It is also possible to employ more than one radiation sensor 30.

In a situation where the radiation sensor 30, the supporting plate 31, and the like are removed from the space between the irradiation apparatus 20 and the imaging stand 1, for example, the distance SID between the focal point F of the radiation source of the irradiation apparatus 20 and the cassette-type detector D installed in the imaging stand 1 is measured at the time of or prior to imaging. Here, the distance SID may be measured by the above described measurement technique or may be measured by some other method. At the time of imaging, the diaphragm of the collimator 21 of the irradiation apparatus 20 is automatically adjusted by the irradiation apparatus 20 or is manually adjusted by a radiological technologist or the like watching the visible light emitted from the irradiation apparatus 20 as in conventional cases. In this manner, the radiation field is adjusted so that radiation is appropriately emitted to the patient as the subject H.

In that situation, the patient as the subject H is temporarily removed from the position in front of the imaging stand 1, and the irradiation apparatus 20 is caused to emit radiation (the amount of the radiation emitted here is a radiation dose that can be detected by the radiation sensor 30). The radiation sensor 30 is then moved two-dimensionally or one-dimensionally, and the vertical range and the horizontal range of the radiation emitted from the irradiation apparatus 20 are measured. When actual imaging is performed with radiation emitted to the subject H, an image of the subject H and others is captured by the depth camera 23 or some other imaging unit.

Figure 22:
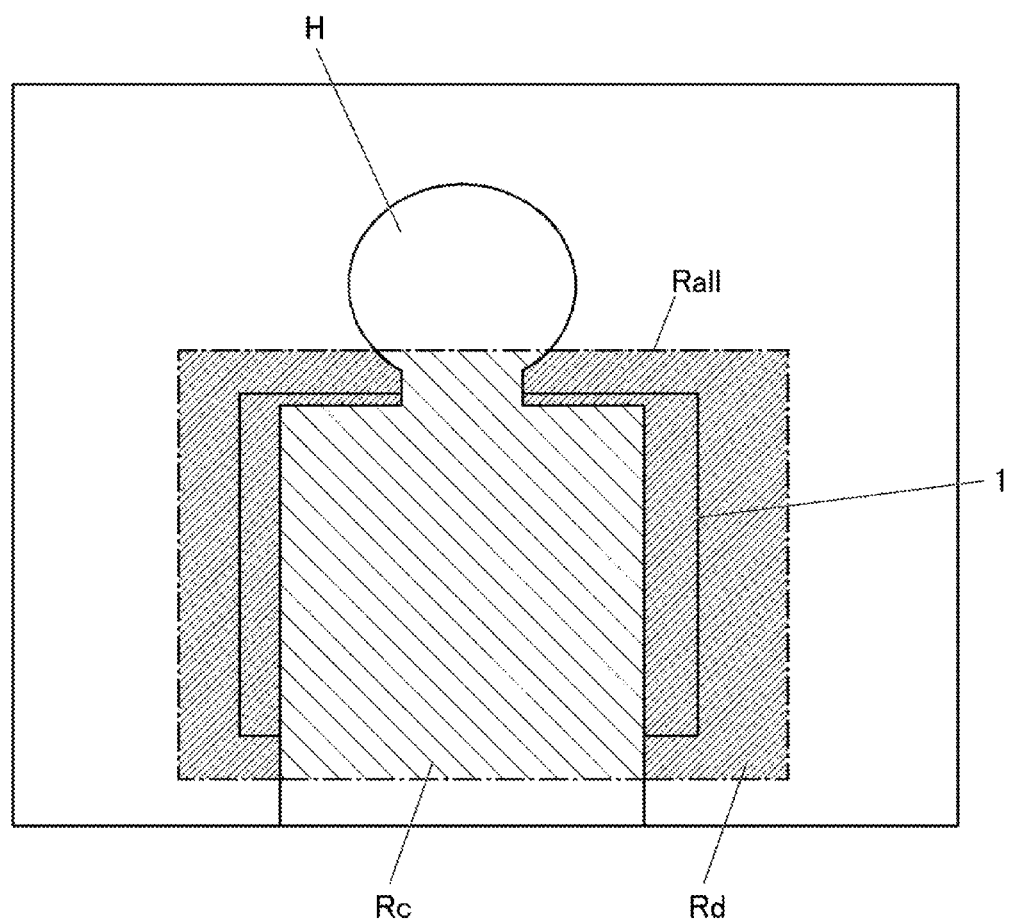
FIG. 22 is a diagram showing a radiation range Rall defined in a captured image, a region Rc of the imaged subject, and a region Rd outside the imaged subject.

As described above, the distance SID between the focal point F of the radiation source of the irradiation apparatus 20 and the cassette-type detector D installed in the imaging stand 1 has been measured and is already known, and the distance rs between the radiation sensor 30 and the focal point F of the radiation source of the irradiation apparatus 20 is also already known. Accordingly, based on the emitted radiation ranges measured in the above described manner, it is possible to identify the radiation range Rall at the distance SID from the focal point F of the radiation source of the irradiation apparatus 20 (or the distance SID at which the cassette-type detector D is located) in the captured image, as shown in FIG. 22.

As a result of an analysis of the image, the area of the region Rc of the imaged subject H and the area of the region Rd outside the imaged subject H can be calculated. Accordingly, the actual dose of radiation to which the patient as the subject H has been exposed can be accurately calculated by multiplying the dose area product measured with the DAP meter by Rc/(Rc+Rd).

As described above, with the above described structure (see FIG. 21) newly developed by the inventor, it is possible to accurately calculate the actual dose of radiation to which the patient as the subject has been exposed (or the dose area product of radiation actually emitted to the patient). Accordingly, the actual dose of radiation to which the patient has been exposed is accurately recognized, and the patient is prevented from being exposed to a larger dose area product of radiation than necessary. Thus, the dose of radiation to which the patient is exposed can be reduced.

[Increasing Power while Minimizing the Focal Point of the Radiation Source]

Figure 23A:
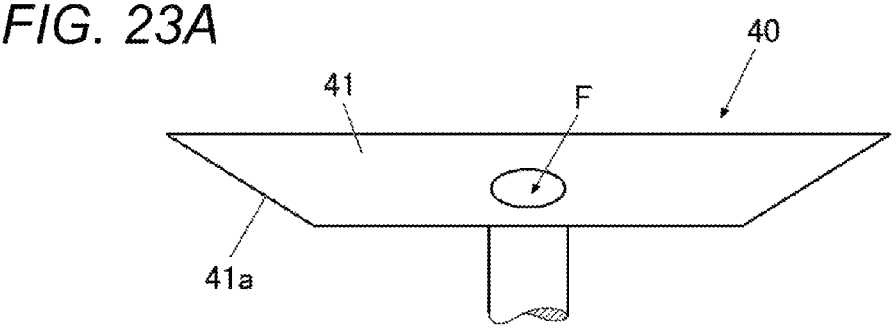
FIG. 23A is a front view of the radiation source of a conventional irradiation apparatus, for explaining the structure and the focal point of the radiation source.
Figure 23B:
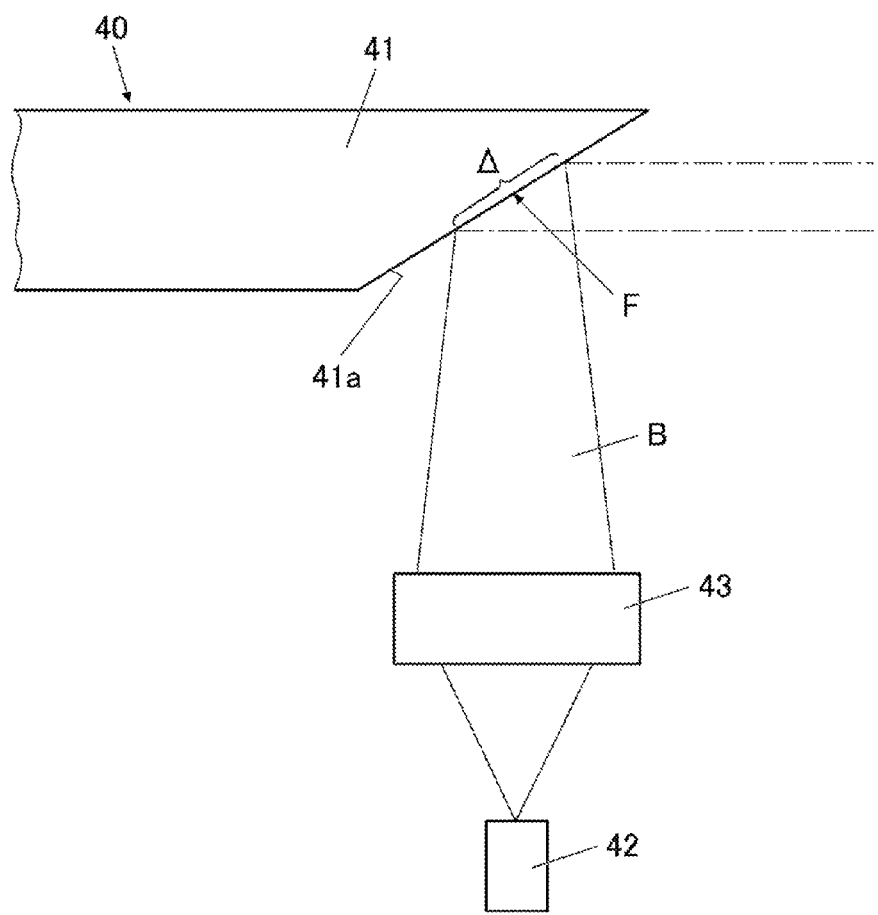
FIG. 23B is a side view of the radiation source.

In the irradiation apparatus 20 (see FIG. 18 and others) that emits radiation to a panel D (or a cassette-type detector D such as an FPD cassette or a CR cassette) installed in the imaging stand 1, the radiation source 40 or the like that generates radiation is provided as described above. As shown in FIGS. 23A and 23B, for example, the radiation source 40 is designed to generate radiation such as X-rays at the focal point F by emitting an electron beam B from an electron gun 42 located below the focal point F, toward a region in a tilted surface 41a of a rotating anode 41 or toward the focal point F.

FIG. 23A is a view of the rotating anode 41 and other components of the radiation source 40, seen from the subject. FIG. 23B is a view of the rotating anode 41 and other components, seen from the left in FIG. 23A. In FIGS. 23A and 23B, the size of the focal point F is very large in relation to the size of the rotating anode 41 and other components, for easier visual recognition of the shape of the focal point F. The same applies in the respective drawings to be later referred to. Therefore, the electron beam B shown in FIG. 23B is not much narrowed by an electron lens 43, for example. In reality, however, the electron beam B is narrowed so that the diameter of the focal point F becomes several hundreds of μm, for example. Furthermore, it goes without saying that the electron beam B is not reflected at the position of the focal point F on the tilted surface 41a of the rotating anode 41, but the focal point F irradiated with the electron beam B serves as the source of radiation emission. Accordingly, radiation is emitted in all directions from the focal point F, and is collimated by the above described collimator, so that the radiation is emitted forward in FIG. 23A (and rightward in FIG. 23B), for example.

If the extent of the focal point F is too large, an image captured through emission of radiation from the radiation source 40 to the panel D via the subject is blurred. Therefore, the radiation source 40 is required to reduce the extent of the focal point F, or to make the focal point smaller.

Figure 24:
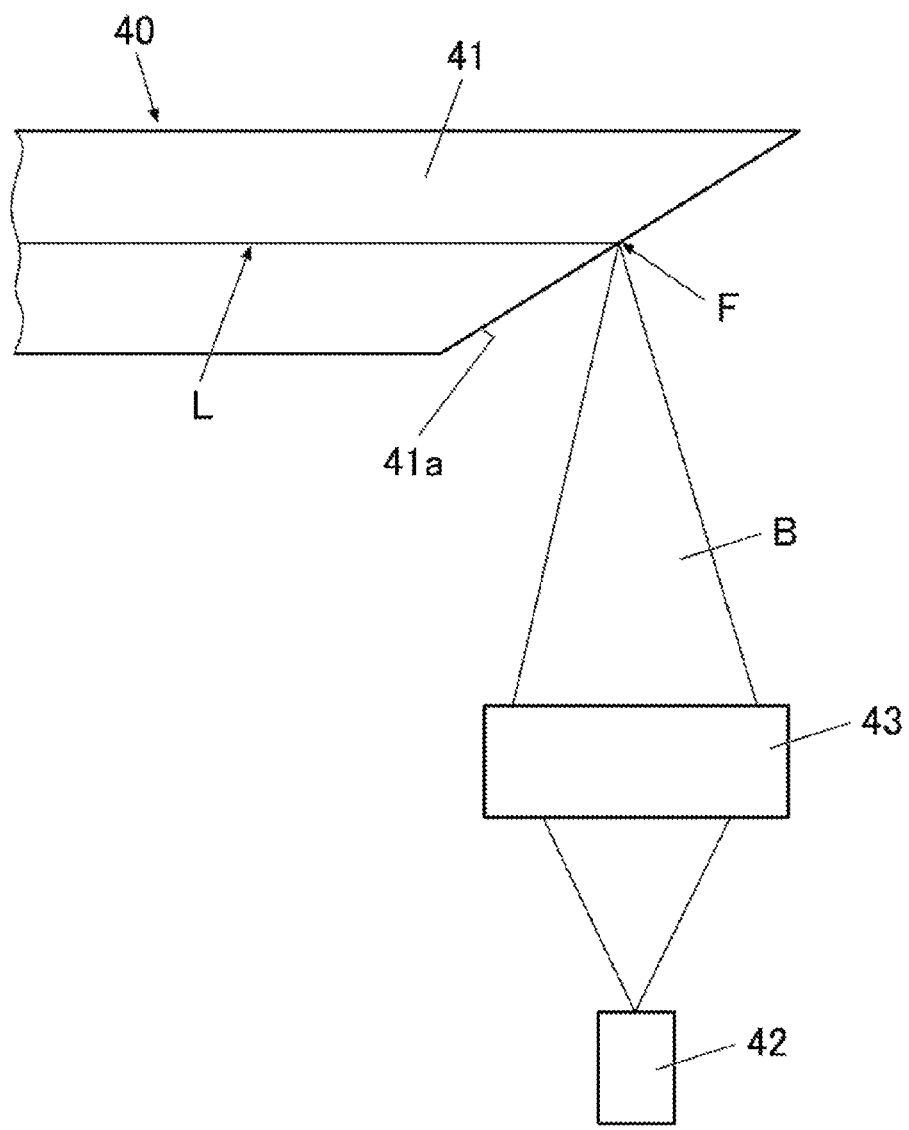
FIG. 24 is a diagram for explaining that, where the focal point is made too small, an electron beam is emitted only to a portion of a tilted surface of the rotating anode, and the portion is linearly damaged.

However, if the focal point F is made too small, only a portion of the tilted surface 41a of the rotating anode 41 that is rotating is irradiated with the electron beam B as shown in FIG. 24, and the portion is linearly damaged (see the line L in FIG. 24), resulting in shortening of the life of the rotating anode 41. Therefore, when the focal point is made smaller, the energy of the electron beam B should be reduced, and the power of the radiation to be emitted from the radiation source 40 needs to be lowered. In a case where the power of the radiation source 40 is to be increased, the focal point F has to be enlarged so as not to damage the tilted surface 41a of the rotating anode 41 as described above. That is, the focal point needs to be made larger.

The electron lens 43 that narrows the electron beam B emitted from the electron gun 42 has limited ability to narrow the electron beam B due to aberration that depends on the energy of the electron beam B. Therefore, at present, the radiation source 40 in many cases is designed to choose between radiation emission to a small-sized focal point at low power and radiation emission to an enlarged focal point at high power.

Figure 25A:
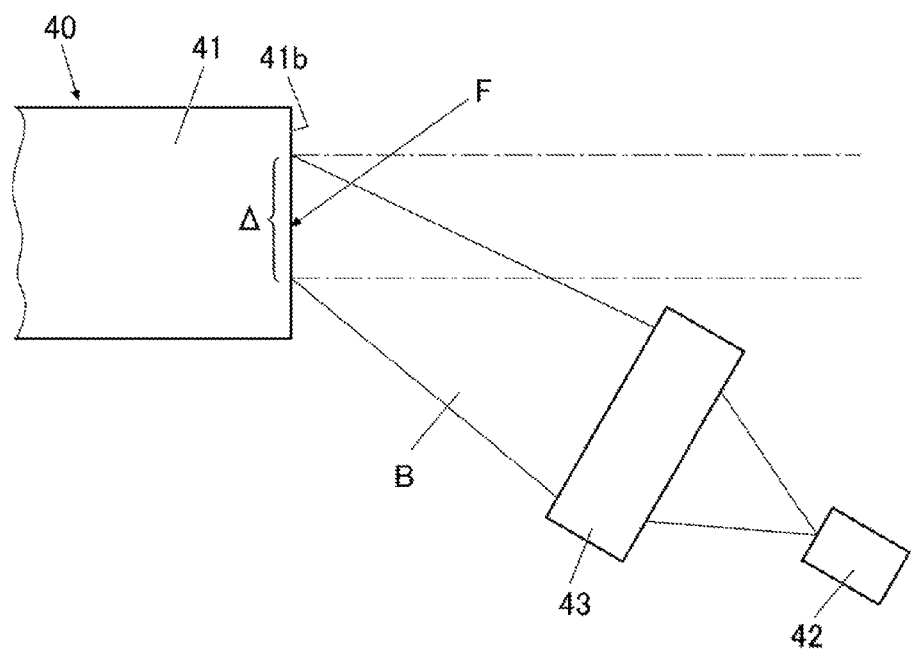
FIG. 25A is a side view of a radiation source, for explaining that the apparent diameter of the focal point becomes larger in the vertical direction if an electron beam is emitted to an non-tilted side surface of the rotating anode.
Figure 25B:
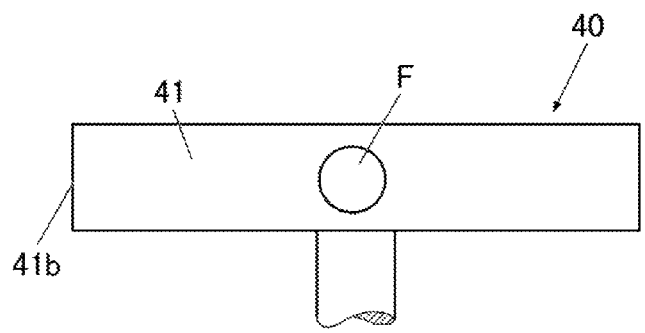
FIG. 25B is a front view of the radiation source.

As shown in FIG. 25A, a side surface 41b of the rotating anode 41 is not tilted (so that the normal line of the side surface 41b extends in the horizontal direction), and an electron beam B having the same diameter as the electron beam B shown in FIG. 23B is emitted to the side surface 41b. As a result, the apparent diameter of the focal point F in the vertical direction becomes larger as shown in FIG. 25B. On the other hand, where the rotating anode 41 has the tilted surface 41a on which the electron beam B is to be emitted, and the electron beam is emitted to the tilted surface 41a as shown in FIG. 23B, at least the apparent diameter of the focal point F in the vertical direction can be made smaller as shown in FIG. 23A. It should be noted that the actual diameter A of the focal point F in FIG. 25A is the same as the actual diameter A of the focal point F in FIG. 23B.

As described above, the radiation source 40 at present is devised to make the focal point F smaller at least in the vertical direction even when emitting radiation at high power. However, when radiation is emitted at high power, the focal point F cannot be made smaller in the horizontal direction, and it is still necessary at present to choose between low power with a smaller focal point and high power with a larger focal point.

In view of such circumstances, the inventor made studies on methods and structures for increasing power while reducing the size of the focal point of the radiation source. As a result, the inventor has discovered that this can be realized with the structure described below.

Figure 26A:
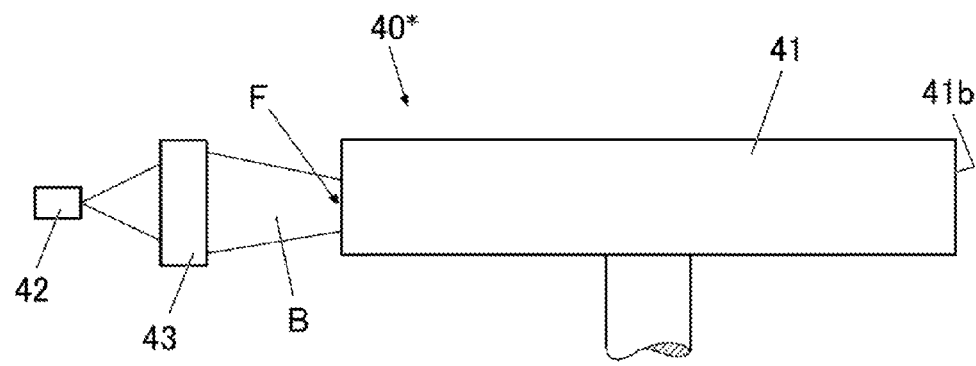
FIG. 26A is a front view of a radiation source newly developed by the inventor.

Specifically, where the rotating anode 41 and other components of the radiation source 40 are seen from the subject, as shown in FIG. 23A, the conventional radiation source 40 or the radiation source 40 at present forms the focal point F by emitting the electron beam B to the center position in terms of the horizontal direction on the rotating anode 41. In a radiation source 40* having a structure newly developed by the inventor, on the other hand, the position in which a focal point F is to be formed is changed to the left edge position (or the right end position; this applies in the description below) of the rotating anode 41 in terms of the horizontal direction, as shown in FIG. 26A. Instead of the tilted surface 41a of the rotating anode 41 of the conventional radiation source shown in FIG. 23A, a non-tilted side surface 41b is formed as the surface of the rotating anode 41 to which the electron beam B is to be emitted, as shown in FIG. 26A.

Figure 26B:
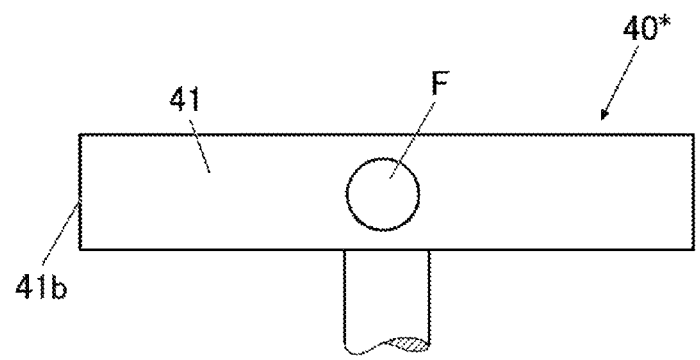
FIG. 26B is a side view of the radiation source.

FIG. 26B shows a state where the rotating anode 41 and other components shown in FIG. 26A are seen from the left in FIG. 26A. The state shown in FIG. 26B is similar to the state shown in FIG. 25B. However, while radiation is emitted forward from the focal point F of the rotating anode 41 in the case shown in FIG. 25B, radiation is emitted rightward in the case shown in FIG. 26B. Also, while radiation is emitted rightward from the focal point F of the rotating anode 41 in the case shown in FIG. 25A, radiation is emitted forward from the focal point F of the rotating anode 41 in the case shown in FIG. 26A.

When seen from the subject to which radiation is to be emitted, as shown in FIG. 26A, the focal point F of the rotating anode 41 of the radiation source 40* appears to be elongated in the vertical direction, and thus, the focal point F is made smaller in the horizontal direction. Furthermore, since the extent of the focal point F is large as shown in FIG. 26B, the energy of the electron beam B emitted to the rotating anode 41 can be made greater. With the above described structure, the radiation source 40* can be made a high-power radiation source, while the focal point F is made smaller in the horizontal direction.

In short, in the radiation source 40* having the structure newly developed by the inventor, the electron beam B with high energy is emitted from the electron gun 42 to a relatively wide region on the side surface 41b of the rotating anode 41 as shown in FIG. 26B, and the power is increased. However, radiation is not emitted in the direction in which the focal point F is seen from the front as shown in FIG. 25B, but radiation is emitted in the direction in which the focal point F is seen from a side as shown in FIG. 26A. With this structure, the apparent diameter of the focal point F is made smaller in the horizontal direction, and the size of the focal point F is made smaller in the horizontal direction. In this manner, in the radiation source 40* having the structure newly developed by the inventor, the power is increased while the size of the focal point F is made smaller in the horizontal direction.

It should be noted that the side surface 41b of the rotating anode 41 of the radiation source 40* does not need to be perpendicular to the upper surface and the lower surface of the rotating anode 41, but may be tilted at an appropriate angle. Although the electron beam B is emitted horizontally to the side surface 41b of the rotating anode 41 in FIG. 26A, the electron beam B may be emitted from above or below to the side surface 41b.

Figure 27:
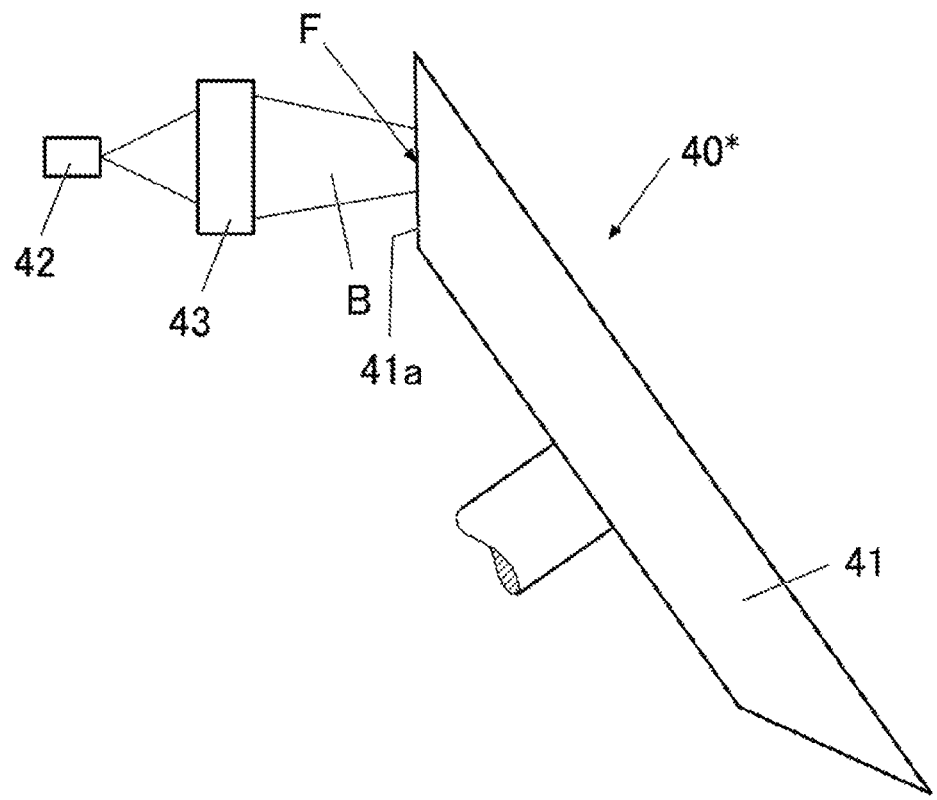
FIG. 27 is a front view of another example of a radiation source having a structure newly developed by the inventor.

Alternatively, as shown in FIG. 27, the rotation axis of the rotating anode 41 may be tilted so that the tilted surface 41a of the rotating anode 41 faces in the vertical direction or an almost vertical direction in the left edge position (or the right edge position) (or the normal line of the tilted surface 41a in that position extends in the horizontal direction or an almost horizontal direction), for example. The electron beam B is then emitted to that position. In FIG. 27, radiation is also emitted forward from the focal point F of the rotating anode 41.

In either case, in the radiation source 40* having a structure newly developed by the inventor, the position of the focal point F formed by emitting the electron beam B to the center position in terms of the horizontal direction on the rotating anode 41 of a conventional radiation source is changed to the left edge position or the right edge position on the rotating anode 41 in terms of the horizontal direction, and the focal point F is formed by emitting the electron beam B to the left edge position or the right edge position on the rotating anode 41 in terms of the horizontal direction, with the rotating anode 41 and other components being seen from the subject (see FIG. 26A and FIG. 27). With this structure, the apparent diameter of the focal point F is made smaller in the horizontal direction, and the size of the focal point F is made smaller in the horizontal direction. At this point, the apparent diameter of the focal point F in the horizontal direction remains small even when the electron beam B with great energy is emitted. Accordingly, the power can be increased while the size of the focal point F is made smaller in the horizontal direction.

Figure 28:
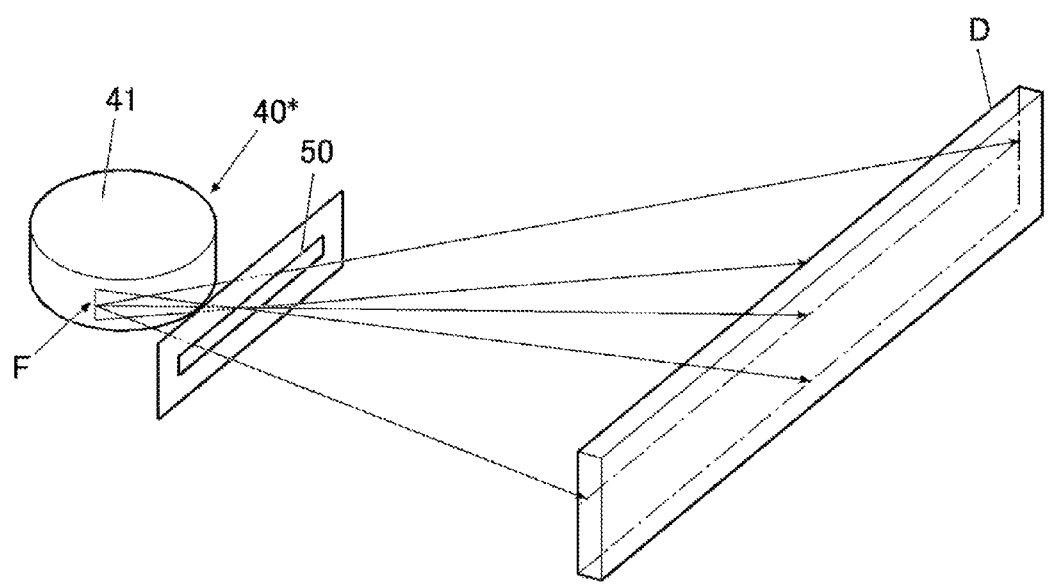
FIG. 28 is a diagram showing an example structure of a line-scanning irradiation apparatus formed with the radiation source shown in FIGS. 26A and 26B.

In the above described structure, the apparent diameter of the focal point F of the rotating anode 41 becomes smaller in the horizontal direction, but neither the diameter nor the apparent diameter of the focal point F becomes smaller in the vertical direction. In view of this, a slit 50 is provided on the output side of the rotating anode 41 of the radiation source 40*, to restrict vertical spread of the radiation emitted from the rotating anode 41, as shown in FIG. 28. In this state, radiation is emitted to the imaging device D via the subject (not shown). In FIG. 28, the focal point F on the rotating anode 41 is shown in the form of a line as a linear light source.

The radiation emitted from the radiation source 40* is then moved in the horizontal direction in the state shown in FIG. 28. In this manner, an irradiation apparatus of a so-called line scanning type can be formed with the use of the radiation source 40*. As described above, in the radiation source 40* having a structure newly developed by the inventor, power can be increased while the size of the focal point F is made smaller in the horizontal direction. Accordingly, imaging is performed by emitting high-power radiation with a small-sized focal point from the radiation source 40* of such a line-scanning irradiation apparatus. Thus, a clear, unblurred image of the subject can be captured.

Although the present invention has been described and illustrated in detail, it is clearly understood that the same is by way of illustrated and example only and is not to be taken by way of limitation, the scope of the present invention being interpreted by terms of the appended claims.

What is claimed is:

1. An imaging stand comprising:
a holder having four rectilinear sides and configured to mount therein a cassette-type detector, the cassette-type detector having a radiation incidence surface, the holder being rotatable around a rotation axis perpendicular to the radiation incidence surface, the rotation axis passing perpendicularly through the radiation incidence surface;
a supporting member configured to support the holder from a back surface side of the holder;
a circular gear secured to a shaft member attached to the holder and protruding from a rotation center of the holder, the shaft member extending perpendicularly from a back surface side of the holder, the rotation center of the holder being located in a different position from a position corresponding to the center of the radiation incidence surface of the cassette-type detector held in the holder, the circular gear having a plurality of teeth; and
a linear gear having concavities and convexities to be engaged with the teeth of the circular gear, the linear gear being attached to the supporting member,
wherein, when the holder holding the cassette-type detector is rotated within a first plane around the rotation axis relative to the supporting member, the rotation center of the holder linearly moves within the first plane relative to the supporting member as the holder rotates, the center of the radiation incidence surface does not move by rotation, and a change is caused in orientation and position of the cassette-type detector.

2. The imaging stand according to claim 1, wherein the linear gear is oriented in a second plane parallel to the first plane at a 45 degree angle relative to the sides of the holder, and wherein the linear gear and the circular gear are configured so that, when the holder is rotated around the rotation axis by 90 degrees in a first rotational direction relative to the supporting member to a first position, the center of the radiation incidence surface moves linearly along a first line.

3. The imaging stand according to claim 2, wherein the cassette-type detector held in the holder is a cassette-type detector of 14×17 inches in size, and wherein when the holder is rotated around the rotation axis by 90 degrees in the first rotational direction relative to the supporting member from the first position, the center of the radiation incidence surface moves linearly along a second line perpendicular to the first line.

4. The imaging stand according to claim 1, wherein, when the holder holding the cassette-type detector of 14×17 inches in "portrait" orientation and position is rotated 90 degrees relative to the supporting member, the cassette-type detector of 14×17 inches is placed in "landscape center" orientation and position.

5. The imaging stand according to claim 2, wherein, when the holder holding the cassette-type detector of 14×17 inches in the "portrait" orientation and position is rotated 90 degrees in reverse direction relative to the supporting member, the cassette-type detector of 14×17 inches is placed in "landscape top" orientation and position.

6. The imaging stand according to claim 3, wherein, when the holder is rotated 180 degrees relative to the supporting member, the holder is placed in a position where the cassette-type detector of 17×17 inches can be installed.

7. The imaging stand according to claim 1, further comprising a slide plate slidably mounted to a side of the holder.

8. The imaging stand according to claim 7, further comprising a rod-shaped member, a first end of the rod-shaped member being attached to the slide plate, wherein the slide plate is slidably mounted to the holder using the rod-shaped member.

9. The imaging stand according to claim 8, wherein a second end of the rod-shaped member is attached to the supporting member.

10. The imaging stand according to claim 9, wherein the rod-shaped member and the slide plate are configured so that, when the holder is rotated, the slide plate moves relative to the holder.

* * * * *